United States Patent
Hamilton et al.

(10) Patent No.: US 7,608,581 B2
(45) Date of Patent: Oct. 27, 2009

(54) BIOFUNCTIONAL, ANTIMICROBIAL COATINGS FOR MEDICAL DEVICES

(75) Inventors: Paul Hamilton, Cary, NC (US); Daniel Kenan, Chapel Hill, NC (US); Mark Grinstaff, Boston, MA (US)

(73) Assignee: Affinergy, Inc., Durham, NC (US)

( * ) Notice: Subject to any disclaimer, the term of this patent is extended or adjusted under 35 U.S.C. 154(b) by 0 days.

(21) Appl. No.: 11/638,973

(22) Filed: Dec. 14, 2006

(65) Prior Publication Data

US 2007/0104758 A1    May 10, 2007

Related U.S. Application Data

(63) Continuation-in-part of application No. PCT/US2005/021147, filed on Jun. 15, 2005.

(60) Provisional application No. 60/651,747, filed on Feb. 10, 2005, provisional application No. 60/651,338, filed on Feb. 9, 2005, provisional application No. 60/580,019, filed on Jun. 16, 2004.

(51) Int. Cl.
    *C07K 14/00* (2006.01)
(52) U.S. Cl. .............................. 514/2; 530/300; 530/350
(58) Field of Classification Search ........................ None
    See application file for complete search history.

(56) References Cited

U.S. PATENT DOCUMENTS

| | | | |
|---|---|---|---|
| 4,442,133 A * | 4/1984 | Greco et al. ............... 427/2.25 |
| 5,217,493 A * | 6/1993 | Raad et al. ............... 623/11.11 |
| 5,520,664 A | 5/1996 | Bricault et al. |
| 5,624,704 A | 4/1997 | Darouiche et al. |
| 5,681,575 A | 10/1997 | Burrell et al. |
| 5,709,672 A | 1/1998 | Illner |
| 5,847,047 A | 12/1998 | Haynie et al. |
| 5,902,283 A | 5/1999 | Darouiche et al. |
| 6,261,271 B1 | 7/2001 | Solomon et al. |
| 6,361,526 B1 | 3/2002 | Reisdorf et al. |
| 7,208,011 B2 | 4/2007 | Shanley et al. |
| 7,238,669 B2 | 7/2007 | Bishop-Hurley et al. |
| 7,282,214 B2 | 10/2007 | Willcox et al. |
| 2002/0198590 A1 | 12/2002 | Ung-Chhun |
| 2003/0185870 A1 | 10/2003 | Grinstaff et al. |
| 2003/0203038 A1 | 10/2003 | Vail |
| 2004/0029782 A1 * | 2/2004 | Meyer et al. ................... 514/7 |
| 2004/0127640 A1 | 7/2004 | Belcher et al. |
| 2005/0085623 A1 | 4/2005 | Balian |
| 2005/0187162 A1 | 8/2005 | Dhanaraj et al. |
| 2006/0123505 A1 | 6/2006 | Kikuchi et al. |
| 2007/0104758 A1 | 5/2007 | Hamilton et al. |
| 2007/0160644 A1 | 7/2007 | Kenan et al. |

FOREIGN PATENT DOCUMENTS

WO    2001056627    *    8/2001

OTHER PUBLICATIONS

Collin; "Decreasing catheter colonization through use of an antiseptic-impregnated catheter"; *Chest*, vol. 115, No. 6, pp. 1632-1640, 1999.
Written Opinion for the International Searching Authority for PCT/US08/80321, Mar. 17, 2009.
Written Opinion of the International Searching Authority for PCT/US08/61200, Sep. 29, 2008.

* cited by examiner

*Primary Examiner*—Karen Cochrane Carlson
(74) *Attorney, Agent, or Firm*—Laura L. Kiefer; M. Bud Nelson

(57) ABSTRACT

The present invention provides compositions and methods for an improved coating for medical devices. Provided is an interfacial biomaterial or biofunctional coating composition comprising at least one binding domain that has bind specificity for a surface material of a medical device, and at least one binding domain that has binding specificity for an antimicrobial composition. Methods for coating a surface of a medical device, and for manufacturing of a medical device, comprise contacting the surface to be coated with the biofunctional coating material in an amount effective to form a coating.

15 Claims, No Drawings

BIOFUNCTIONAL, ANTIMICROBIAL COATINGS FOR MEDICAL DEVICES

CROSS REFERENCE TO RELATED APPLICATIONS

This is a continuation-in-part of International Application PCT/US2005/021147 with an International filing date of 15 Jun. 2005, published in English under PCT Article 21(2) and abandoned on 17 Dec. 2006; and a nonprovisional application which claims the benefit of: U.S. Provisional Application No. 60/580,019, filed Jun. 16, 2004; U.S. Provisional Application No. 60/651,338, filed Feb. 9, 2005; and U.S. Provisional Application No.60/651,747, filed Feb. 10, 2005, each of which is hereby incorporated by reference herein.

FIELD OF THE INVENTION

This invention relates to the coating of medical devices with a biofunctional coating composition comprising a peptide that binds specifically to the surface of the medical device, and a peptide which binds specifically to an antimicrobial composition.

BACKGROUND OF THE INVENTION

The problems associated with adherence and growth of bacteria on medical devices are well know. For example, catheterization with a "central line catheter" involves placing a polyurethane or polyvinylchloride hose into a blood vessel in the patient's chest while the other end of the hose remains exposed to the hospital room environment and therefore to a variety of pathogens, potentially including drug-resistant pathogens. Frequently, this catheterization results in the life-threatening complication of system-wide infection of the blood. Research suggests that up to 90% of such cases originate in films of bacteria that adhere to catheter walls.

Other types of catheters that are frequently used include urinary catheters, which are typically used with incontinent elderly patients, and are typically made of silicone and latex. Unfortunately, virtually all patients who have urinary catheters in place for 28 days or more develop urinary tract infections. Nearly all hospital-acquired systemic infections that are not associated with central line catheters are associated with urinary catheters. Treatment of urinary catheter-associated infections alone costs an estimated $1.8 billion annually.

Similar problems currently exist with orthopedic implants. Main causes of orthopedic implant failure include host inflammatory responses, and infection due to the formation of bacterial biofilms on the surface of the implants. Furthermore, studies have shown that infections are very common at the site of pin insertion, and infection associated with external fixators may be as high as 85%. Because metal pins and wires are being used more often in the treatment of orthopedic trauma, primarily for external fixation of bone fractures, any device improvements that decrease the rate of infections from joint prostheses or other metallic implants could have a significant impact on the quality of orthopedic healthcare. Likewise, for ophthalmic devices, particularly contact lenses, microorganisms can adhere to the device during normal handling and wear, and even contaminate the storage container and/or solutions for cleaning or rehydrating such devices. While storage solutions have been developed to disinfect the device, the trend for contact lenses is to extend the period of time which they can be worn without taking them out for storage. Thus, a means directly associated with the ophthalmic device for decreasing the risk of infection, particularly in situations where the device is intended to be worn for more than one day or where it is impractical to remove the device daily for disinfection, is desirable.

A wide variety of surface modifications to medical devices have been tried with a goal of reducing infection rates of the modified medical devices. Such surface modifications include encapsulation of the medical device with a polymer to retard adherence by bacteria, and impregnation or coating of the medical device with antimicrobial agents. Representative examples of patents involving articles that have been coated or impregnated with anti-microbial drugs include U.S. Pat. No. 5,520,664 ("Catheter Having a Long-Lasting Antimicrobial Surface Treatment"), U.S. Pat. No. 5,709,672 ("Silastic and Polymer-Based Catheters with Improved Antimicrobial/Antifungal Properties"), U.S. Pat. No. 6,361,526 ("Antimicrobial Tympanostomy Tubes"), U.S. Pat. No. 6,261,271 ("Anti-infective and antithrombogenic medical articles and method for their preparation"), U.S. Pat. No. 5,902,283 ("Antimicrobial impregnated catheters and other medical implants") U.S. Pat. No. 5,624,704 ("Antimicrobial impregnated catheters and other medical implants and method for impregnating catheters and other medical implants with an antimicrobial agent") and U.S. Pat. No. 5,709,672 ("Silastic and Polymer-Based Catheters with Improved Antimicrobial/Antifungal Properties").

However, the use of known antimicrobial coatings has been reported to have some disadvantages. For example, impregnating catheters with antibiotics may be counter-productive because the concentration of antibiotics released from the catheter inevitably falls, and bacteria are then exposed to sublethal levels of antibiotics. This results in a condition that can promote the development of antibiotic resistance. Coating the surface of a medical device with a polymer often requires special preparation of the surface, and multi-step chemical procedures. Another disadvantage of current methods to coat medical device surfaces is that, in general, the conditions necessary for attachment of the coating threaten to modify the relatively labile chemical groups or macromolecular folds that are typically desired for attachment of bioactive agents such as antimicrobial agents. The extra steps and costs necessary to preserve the function of bioactive agents in a surface coating often render the project cost-prohibitive.

Thus, the need remains in the art for a coating that can be applied to the surface of a medical device, wherein the coating inhibits adherence by microorganisms to, and/or growth of microorganisms on, the surface of the coated medical device.

SUMMARY OF THE INVENTION

The present invention provides materials, compositions, and methods for an improved coating for surfaces of medical devices including, but not limited to, implants and catheters. The biofunctional coating composition of the present invention is an interfacial biomaterial ("IFBM") which comprises at least one binding domain that specifically binds to a surface of a medical device (for ease of reference, this binding domain is referred to herein as: "surface-binding domain") which is linked (via a linker) to at least one binding domain that specifically binds to an antimicrobial composition (for ease of reference, this binding domain is referred to herein as: "antimicrobial-binding domain"). In another embodiment, the biofunctional coating composition comprises at least one surface-binding domain linked to at least one antimicrobial-binding domain, wherein the at least one antimicrobial binding domain is bound to one or more antimicrobial compositions. As will be described herein in more detail, in one embodiment the interfacial biomaterial comprises an antimicrobial-binding domain that binds to an antibiotic of a single class of antibiotics. In another embodiment, the biofunctional coating composition of the present invention comprises more than one type of antimicrobial-binding domain, with each type binding a different antimicrobial composition. For example, the biofunctional coating composition may contain a first antimicrobial-binding domain which binds to an aminoglycoside, such as vancomycin; and a second antimicrobial-binding domain which binds to a different class of antibiotics, for example, from the class of penicillins, such as oxacillin. The compositions and methods of the invention are for improving the performance of medical devices, for example, by conferring antimicrobial activity to the medical device by preventing or inhibiting unwanted adherence and/or growth of microbes on the surface of a medical device coated by the bifunctional coating composition according to the present invention. Also provided by the present invention is a surface of a medical device coated by the interfacial biomaterial of the present invention.

DETAILED DESCRIPTION OF THE INVENTION

The present invention provides compositions for an improved coating for medical devices, methods of coating medical devices using those compositions, and a surface of a medical device which is coated with a biofunctional coating composition of the present invention.

Definition Section While the following terms are believed to be well understood by one of ordinary skill in the art, the following definitions are set forth to facilitate explanation of the invention.

The term "antimicrobial activity" is used, for purposes of the specification and claims, to refer to the ability of a composition (including a compound or agent) to inhibit or irreversibly prevent microbial growth. Such inhibition or prevention can be through a microbicidal action (the ability of the composition to kill, or irrevocably damage one or more target micoorganisms), or through a microbiostatic action (the ability of the composition to inhibit the growth of one or more target micoorganisms without death of the one or more target microorganisms), or via a combination thereof (e.g., if a combination of antimicrobial compositions are used, with one or more being microbicidal, and one or more being microbiostatic). Microbicidal or microbiostatic action can be applied therapeutically (to an environment either presently exhibiting microbial growth), or prophylactically (to an environment at risk of sustaining or supporting such growth). When referring to the antimicrobial activity conferred or imparted to a medical device coated by a biofunctional coating according to the present invention, the primary activity is the ability to inhibit and/or prevent microbial growth to the coated surface; however, as a result of or in addition to this primary activity, the biofunctional coating composition according to the present invention may also inhibit or reduce any one or more of adherence of microorganisms to, or biofilm formation on, a surface of the medical device coated by a biofunctional coating composition according to the present invention.

The term "antimicrobial composition" is used, for purposes of the specification and claims, to refer to a composition (including a compound or agent) having antimicrobial activity. For example, a preferred antimicrobial composition is an antibiotic. Antibiotics are known in the art to comprise several distinct types (classes) based on similarities in chemical structure, composition, and/or function. Classes of antibiotics are known to include, but are not limited to, penicillins (e.g., penicillin G, penicillin V, ampicillin, methicillin, oxacillin, amoxicillin, amoxicillin-clavulanate, ticarcillin, nafcillin, cloxacillin, piperacillin-tazocbactam, and dicloxacillin), cephalosporins and cephams (e.g., cefazolin, cefuroxime, cefotaxime, ceftriaxone, ceftazidime, cefixime, cefpodoxime, ceftibuten, cefdinir, cefaclor, cefprozil, loracarbef, cefadroxil, cephalexin, cephradineze, cefepime, cefpirome, cefataxidime pentahydrate, ceftazadime, cefteram, cefotiam, cefamandole, cefotetan, cefalexin, cefaparin, cefbuperazone, cefcapene, cefditoren, ceftamet, cefnetrazole, cefminox, cefoperazone, ceforanide, cefotiam, cefoxitin, cefpimazole, cefpiramide, cefradine, cefroxadine, cefsulodin), aminoglycosides (e.g., amikacin, gentamycin, tobramycin, netromycin, streptomycin, kanamycin, paromomycin, neomycin), oxazolidinones (e.g., linezolid), streptogramins (e.g., quinupristin, dafopristin, synercid, pristinamycin), sulfonamides (e.g., co-trimoxazole, sulfamethoxasol, sulfadiazine, sulfadoxine, trimethoprim), tetracyclines (tetracycline, demeclocycline, minocycline, doxycycline), macrolides (erythromycin, clarithromycin, azithromycin, axithromycin, dirithromycin, troleandomycin, oleandomycin, roxithromycin, telithromycin), carbapenems (imipenem, meropenem, ertapenem, panipenem/betamipron), ketolides, fluoroquinolones/quinolones (e.g., ciprofloxacin, levofloxacin, ofloxacin, gatifloxacin, norfloxacin, lomefloxacin, trovafloxacin, moxifloxacin, sparfloxacin, gemifloxacin, pazufloxacin), and glycopeptides (e.g., vancomycin, teicoplanin, daptomycin, oritavancin). A preferred antimicrobial composition may be used with the present invention to the exclusion of an antimicrobial composition other than the preferred antimicrobial composition.

The term "medical device", used herein for purposes of the specification and claims, refers to any article used as an implant in the body of an individual (including both human and non-human individuals) (examples of implantable medical devices include but are not limited to: prosthetic joints, plates, screws, pins, nails, rivets, bone fixation implants, and artificial ligaments and tendons); any article used as a conduit (e.g., a catheter, tubing (e.g., endotracheal tube, chest tube, and the like)) related to medical treatment or for biological materials (e.g., tubes for feeding, tubes for draining biological fluids); or any container used as a storage device for biological materials (e.g., biological fluid collection bags, devices for storing proteins or solutions containing cells, and the like). A preferred medical device comprises a vascular device (also known as "intravascular device"). Representative vascular devices include, but are not limited to, stents, patches (e.g., heart patches), valves, annuloplasty rings, annular rings, mechanical assist devices, vascular sealing devices, peripheral venous catheters, central venous catheters, arterial catheters, pacemakers, defibrillators, guidewires, embolic protection filters and devices, implantable infusion pumps, and vascular grafts. Another preferred medical device includes ophthalmic devices, particularly contact lenses (including, but not limited to, soft contact lenses ("daily wear" and "extended wear"), rigid lenses), intraocular lenses, scleral lenses, overlay lenses, ocular inserts, and optical inserts. A preferred medical device (including its surface or surface material thereof) may be used with the present invention to the exclusion of a medical device other than the preferred medical device.

A medical device may be comprised of, and hence have one or more surfaces comprised of, a variety of materials including, but not limited to, a metal, a metal oxide, a non-metal oxide, a ceramic, a rubber, a plastic, an acrylic, a silicone, a polymer, and combinations thereof. Metals used in the manufacture of medical devices are known in the art to include, without limitation, stainless steel, tantalum, gold, platinum, silver, tungsten, titanium, titanium alloys (for example, memory titanium alloys such as nitinol), a transition metal, alkali metals, and alkaline earth metals (the latter three metals are Groups chosen from the Periodic Table). Metal alloys (e.g., cobalt-chrome alloy) and metal oxides of each of these groups, individually and separately, are included. Polymers may be used in the manufacture of a medical device and/or may be applied to a medical device as a coating of the medical device; hence, a polymer may be a surface of a medical device. Generally, hydrophilic polymers are polymers chosen for coating a medical device to form a coated surface. Polymers used for medical devices may be biodegradable (e.g., self-dissolving, bioresorbable, degradable in vivo) or non-biodegradable.

Non-limiting examples of suitable biodegradable polymers include: poly-amino acids; polyanhydrides including maleic anhydride polymers; polycarboxylic acid; polyethylene oxide; one or more of polylactic acid or polyglycolic acid (and copolymers and mixtures thereof, e.g., poly(L-lactic acid) (PLLA), poly(D,L,-lactide), poly(lactic acid-co-glycolic acid), 50/50 (DL-lactide-co-glycolide)); polyorthoesters; polydioxanone; polyphosphazenes; polypropylene fumarate; polydepsipeptides; one or more of polycaprolactone (and co-polymers and mixtures thereof, e.g., poly(D,L-lactide-co-caprolactone) or polycaprolactone co-butylacrylate; polyhydroxybutyrate valerate and blends; polycarbonates (e.g., tyrosine-derived polycarbonates and arylates), polyiminocarbonates, polydimethyltrimethylcarbonates; cyanoacrylate; calcium phosphates; polyglycosaminoglycans; macromolecules (such as polysaccharides, e.g., hyaluronic acid, cellulose, hydroxypropylmethyl cellulose); proteins and polypeptides (e.g., gelatin, collagen, albumin, and the like); and mixtures and copolymers of any of the foregoing.

Non-limiting examples of suitable non-biodegradable polymers include: inert polyaryletherketones, including polyetheretherketone ("PEEK"), polyether ketone, polyetherketoneketone, and polyetherketoneetherketoneketone; polyurethanes; polystyrene, and styrene-ethylene/butylene-styrene block copolymers; polyisobutylene copolymers and styrene-isobutylene-styrene block copolymers; polyvinylpyrrolidone; polyvinyl alcohols; copolymers of vinyl monomers; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene; copolymers of ethylene and polypropylene; polycarbonates, silicones; siloxane polymers; cellulosic polymers (e.g, cellulose acetate); and mixtures, and copolymers (including cross-linked copolymers) of any of the foregoing.

Hydrophilic polymers are also a preferred composition for soft contact lenses. Such polymers are known in the art to include, but are not limited to, flexible, soft silicone or hydrophilic silicone elastomers; suitable hydrogel-forming polymeric materials, for example, hydroxyethyl methacrylate-based materials, or silicone-hydrogel materials; gas permeable materials; or other ophthalmically compatible lens materials; and combinations thereof.

When the term "surface" is used herein in conjunction with a medical device, generally it is referring to one or more surfaces of the medical device which is or becomes exposed to biological solutions and/or biological tissue; and hence, such surface is susceptible to microbial growth, adherence, and/or biofilm formation.

The term "surface-binding domain", used herein for purposes of the specification and claims, refers to a peptide that binds to a surface of a medical device; and more particularly, a peptide having binding specificity for a material comprising the surface of a medical device to be coated. In a preferred embodiment, the surface-binding domain is identified for binding specificity (with affinity) sufficient for its intended purpose (as know to those skilled in the art) by screening and/or selection methods known in the art, such as from phage display libraries. Non-limiting examples of surface-binding domains are illustrated in Tables 1 & 2, and are represented by amino acid sequences set forth in SEQ ID NOs: 1-94. A preferred surface-binding domain (including the type of surface to which it binds with specificity) may be used with the present invention to the exclusion of a surface-binding domain other than the preferred surface-binding domain.

The term "antimicrobial-binding domain", used herein for purposes of the specification and claims, refers to a peptide that binds to an antimicrobial composition (the latter may consist of a specific antimicrobial composition, or may comprise more than one antimicrobial composition of the same class (e.g., of shared structure and/or function) as previously described herein in more detail), and more particularly a peptide having binding specificity for an antimicrobial composition. An antimicrobial-binding domain can comprise a binding domain comprising dipeptides and tripeptides found in nature to bind to an antimicrobial composition. For example, the dipeptide (D-Ala-D-Ala) and tripeptide (Lys-D-Ala-D-Ala) are known binding domains found in nature having binding specificity for the vancomycin family of antibiotics. In a preferred embodiment, the antimicrobial-binding domain is identified for binding specificity (with affinity) sufficient for its intended purpose (as know to those skilled in the art) by screening and/or selection methods known in the art, such as from phage display libraries. Non-limiting examples of antimicrobial-binding domains are illustrated in Table 3, and may be represented by amino acid sequences set forth in SEQ ID NOs: 95-133. A preferred antimicrobial-binding domain (including the type of antimicrobial composition to which it binds with specificity) may be used with the present invention to the exclusion of an antimicrobial-binding domain other than the preferred antimicrobial-binding domain.

In an alternate embodiment, an antimicrobial-binding domain used in the biofunctional coating composition of the present invention itself has antimicrobial activity in addition to, or instead of, having binding specificity for an antimicrobial composition. Examples of biologically active peptides having antimicrobial activity that may be suitable for use in accordance with the present invention are well known in the art (e.g., indolicidin, defensins (beta or alpha), cathelicidin, plectasin, caerin, maculatin, KIK peptides (so called because of the prevalence of lysine (K) and isoleucine (I) in their amino acid sequences), magainin, gramicidin, NK-2, dermaseptin, defensin, bacteriocin, pleurocidin, LL-37, halocidin, dermicidin, mucocidin, heparin-binding protein peptide, and the like), the amino acid sequences of which are in the public domain (published literature and/or known protein databases). Preferably the peptide, or a biologically active analog thereof, has in its amino acid sequence one or more amino acids having an acidic side chain (e.g., Asp (D), Glu (E), or a combination thereof), which may be of assistance to the surface-binding domain in anchoring the biofunctional coating composition to the surface to be coated.

The terms "biofunctional coating composition" and "interfacial biomaterial" are used interchangeably, in reference to the present invention and for purposes of the specification and claims, to refer to a composition comprising at least one surface-binding domain and at least one antimicrobial-binding domain, wherein the surface-binding domain and antimicrobial-binding domain are coupled together (e.g., by one or more of physically, chemically, synthetically, or biologically (e.g., via recombinant expression)) in such a way that each binding domain retains its respective function to bind to the respective molecule for which it has binding specificity. For example, using standard reagents and methods known in the art of peptide chemistry, a peptide of a surface-binding domain can be covalently coupled directly to a peptide of an antimicrobial-binding domain via a side chain-to-side chain bond (e.g., where each of the peptides have a side chain amine (e.g., such as the epsilon amine of lysine)), a side chain-to-N terminal bond (e.g., coupling the N-terminal amine of one peptide with the side chain amine of the other peptide), a side chain-to-C-terminal bond ((e.g., coupling the C-terminal chemical moiety (e.g., carboxyl) of one peptide with the side chain amine of the other peptide), an N-terminal-to-N-terminal bond, an N-terminal to C-terminal bond, a C-terminal to C-terminal bond, or a combination thereof. In synthetic or recombinant expression, a peptide of a surface-binding domain can be coupled directly to a peptide of an antimicrobial-binding domain by synthesizing or expressing both peptides as a single peptide. The coupling of surface-binding domain to an antimicrobial-binding domain may also be via a linker to form a biofunctional coating composition.

The biofunctional coating composition or interfacial biomaterial of the present invention comprises: (a) the at least one surface-binding domain in an amount effective to mediate the binding of the biofunctional coating composition or interfacial biomaterial to the surface material (e.g., metal, plastic, or polymer) of the medical device for which the at least one surface-binding domain has binding specificity; and (b) the at least one antimicrobial-binding domain having bound thereto an antimicrobial composition in an amount effective to confer antimicrobial activity to the coated medical device; wherein the at least one surface-binding domain and the at least one antimicrobial-binding domain are coupled together. In a preferred embedment, a linker is used to join together the at least one surface-binding domain and the at least one antimicrobial-binding domain.

In function, when the biofunctional coating composition is applied to a surface of a medical device, binding of the biofunctional coating composition to the surface is mediated primarily by a domain of the biofunctional coating composition comprising the surface-binding domain; and the antimicrobial properties of, or associated with, the biofunctional coating composition is mediated primarily by one or more antimicrobial compositions bound to a domain of the biofunctional coating composition comprising the antimicrobial-binding domain. Thus, when a medical device is coated with a biofunctional coating composition of the present invention, and then the coated medical device is introduced into or applied to an individual, the biofunctional coating composition is then the interface (hence, "interfacial biomaterial") between the medical device and the biological tissues and/or biological fluids of the individual. Accordingly, provided is a method of conferring antimicrobial activity to a medical device comprising coating one or more surfaces of the medical device with a biofunctional coating composition or interfacial biomaterial comprising at least one surface-binding domain and at least one antimicrobial-binding domain, wherein the at least one surface-binding domain and the at least one antimicrobial binding domain are coupled together. In another embodiment, provided is a method of conferring antimicrobial activity to a surface of a medical device, the surface being suitable for contacting one or more of a biological tissue and a biological fluid, the method comprising coating one or more surfaces of the medical device with a biofunctional coating composition or interfacial biomaterial comprising at least one surface-binding domain and at least one antimicrobial-binding domain, wherein the at least one surface-binding domain and the at least one antimicrobial binding domain are coupled together, and wherein the at least one antimicrobial binding domain is bound to one or more antimicrobial compositions.

It is an important feature of the biofunctional coating compositions of the present invention that the biofunctional coating composition may be comprised of a single type ("type" as defined by binding specificity) of surface-binding domain (e.g., a peptide having binding specificity for a certain metal, such as titanium), or may be comprised of more than one type of surface-binding domain (i.e., different peptides, each with a different binding specificity; for example, one type of surface-binding domain which has binding specificity for a selected metal, and another type of surface-binding domain which has binding specificity for a selected polymer). Thus, each type of surface-binding domain is capable of binding to a different surface material. The surface-binding domain in the biofunctional coating composition of the present invention is selected to specifically bind (e.g., typically, noncovalently, ionically, or electrostatically) to the surface material or component of the medical device desired to be coated. In that regard, having more than one type of surface-binding domain in a biofunctional coating composition of the present invention is particularly useful for a medical device which comprises more than one type of material (or surface component) exposed to a biological tissue and/or biological fluid (e.g., a surface comprised of plastic, and a surface comprised of a metal or metal oxide, or alloy; or a surface comprised of a polymer coating, and a surface comprised of a metal or metal oxide or alloy; or two or more surfaces, each comprised of a different metal or metal oxide or alloy). Similarly, the biofunctional coating compositions of the present invention may comprise a single type ("type" as defined by binding specificity) of antimicrobial-binding domain (e.g., a peptide having binding specificity for a certain antimicrobial composition, such as daptomycin), or may comprise of more than one type of antimicrobial-binding domain (e.g., two or more different peptides, each with binding specificity for a different antimicrobial composition). Thus, each type of antimicrobial-binding domain is capable of binding to a different antimicrobial composition. For example, it may be advantageous to have biofunctional coating composition having more than one type of antimicrobial-binding domain so as to result in a combination of antimicrobial compositions (e.g., an antimicrobial composition selected from the class of penicillins, and an antimicrobial composition selected from the class of glycopeptides (e.g., vancomycin)) in the biofunctional coating composition according to the present invention, with the intent to inhibit or prevent growth (and may also inhibit or prevent one or more of adherence or biofilm formation of) bacteria which may be resistant to one of the antimicrobial compositions in the biofunctional coating composition.

The term "linker" is used, for purposes of the specification and claims, to refer to a compound or moiety that acts as a molecular bridge to couple at least two different molecules (e.g., with respect to the present invention, coupling a surface-binding domain to an antimicrobial-binding domain). Thus, for example, one portion of the linker binds to a surface-binding domain according to the present invention, and another portion of the linker binds to an antimicrobial-binding domain. As known to those skilled in the art, and using methods known in the art, a surface-binding domain and an antimicrobial-binding domain may be coupled to the linker in a step-wise manner, or may be coupled simultaneously to the linker, to form a biofunctional coating composition or interfacial biomaterial according to the present invention. There is no particular size or content limitations for the linker so long as it can fulfill its purpose as a molecular bridge, and that the binding specificities of the biofunctional coating composition are substantially retained.

Linkers are known to those skilled in the art to include, but are not limited to, chemical chains, chemical compounds (e.g., reagents), and the like. The linkers may include, but are not limited to, homobifunctional linkers and heterobifunctional linkers. Heterobifunctional linkers, well known to those skilled in the art, contain one end having a first reactive functionality (or chemical moiety) to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), amino acid linkers (typically, a short peptide of between 3 and 15 amino acids, and often containing amino acids such as glycine, and/or serine), and polymers (e.g., polyethylene glycol) may be employed as a linker with respect to the present invention. In some embodiments wherein amino acid linker is chosen, the interfacial biomaterial may be synthesized to be a single, contiguous peptide comprising a surface-binding domain, a linker, and an antimicrobial-binding domain. Thus, the linker attachment is simply via the bonds of the single contiguous peptide.

Suitable polymeric linkers are known in the art, and can comprise a synthetic polymer or a natural polymer. Representative synthetic polymers include but are not limited to polyethers (e.g., poly(ethylene glycol) ("PEG")), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, polyhexanoic acid, flexible chelators such as EDTA, EGTA, and other synthetic polymers which preferably have a molecular weight of about 20 daltons to about 1,000 kilodaltons. Representative natural polymers include but are not limited to hyaluronic acid, alginate, chondroitin sulfate, fibrinogen, fibronectin, albumin, collagen, calmodulin, and other natural polymers which preferably have a molecular weight of about 200 daltons to about 20,000 kilodaltons. Polymeric linkers can comprise a diblock polymer, a multi-block copolymer, a comb polymer, a star polymer, a dendritic or branched polymer, a hybrid linear-dendritic polymer, a branched chain comprised of lysine, or a random copolymer. A linker can also comprise a mercapto (amido)carboxylic acid, an acrylamidocarboxylic acid, an acrlyamido-amidotriethylene glycolic acid, 7-aminobenzoic acid, and derivatives thereof. Linkers are known in the art and include linkers that can be cleaved, and linkers that can be made reactive toward other molecular moieties or toward themselves, for cross-linking purposes.

Depending on such factors as the molecules to be linked, and the conditions in which the linking is performed, the linker may vary in length and composition for optimizing such properties as preservation of biological function, stability, resistance to certain chemical and/or temperature parameters, and of sufficient stereo-selectivity or size. For example, the linker should not significantly interfere with the ability of a surface-binding domain to function in a biofunctional coating composition (i.e., to sufficiently bind, with appropriate avidity for the purpose, to a surface for a medical device for which it has specificity according to the present invention). Likewise, the linker should not significantly interfere with the ability of an antimicrobial-binding domain to function in a biofunctional coating composition (i.e., to sufficiently bind, with appropriate avidity for the purpose, to an antimicrobial composition for which it has specificity according to the present invention). A preferred linker may be a molecule which may have activities which enhance or complement the effect of the biofunctional coating composition of the present invention. For example, using polyethylene glycol or other polymeric molecule or protein (e.g., albumin) as a linker may serve to help prevent non-specific protein and/or undesired cell adherence to the surface of the medical device coated with an interfacial biomaterial according to the present invention. A preferred linker may be used in the present invention to the exclusion of a linker other than the preferred linker.

The terms "binds specifically" or "binding specificity", and like terms used herein, are interchangeably used, for the purposes of the specification and claims, to refer to a binding domain (as described herein) having a higher binding affinity for one target molecule or surface material selected to be bound ("target surface material") over another molecule or surface material (other than the target molecule or target surface material). For example, a surface-binding domain has binding specificity for a stainless steel surface of a medical device, when the surface-binding domain demonstrates preferential binding to stainless steel, as compared to binding to another component or material of the medical device (such as a metal other than stainless steel, or a polymer). Such preferential binding may be dependent upon the presence of a particular conformation, structure, and/or charge on or within the molecule or material for which the binding domain has binding specificity, such that it recognizes and binds to that molecule or material rather than to molecules or materials in general. In some embodiments, a binding domain that binds specifically to a particular surface, material or composition binds at least 10%, 20%, 30%, 40%, 50%, 60%, 70%, 80%, 90%, 100%, 200%, 300%, 400%, 500%, or a higher percentage, more affinity than the binding domain binds to an appropriate control such as, for example, a different material or surface, or a protein typically used for such comparisons such as bovine serum albumin.

The term "peptide" is used herein, for the purposes of the specification and claims to refer to an amino acid chain, wherein the amino acid chain may include naturally occurring amino acids, synthetic amino acids, genetically encoded amino acids, non-genetically encoded amino acids, and combinations thereof. Preferably, the peptide comprising a binding domain according to the present invention comprise a contiguous sequence of no less than about 3 amino acids and no more than about 100 amino acid residues in length, and preferably no less than 7 amino acids and no more than about 60 amino acids in length. A peptide used in accordance with the present invention may be produced by chemical synthesis, recombinant expression, biochemical or enzymatic fragmentation of a larger molecule, chemical cleavage of larger molecule, a combination of the foregoing or, in general, made by any other method in the art, and isolated. The term "isolated" means that the peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes. A preferred peptide may be used in the present invention to the exclusion of a peptide other than the preferred peptide.

Peptides can include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine. Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-imbenzylhistidine.

A peptide according to the present invention may be modified, such as by addition of chemical moieties, or substitutions, insertions, and deletions of amino acids, where such modifications provide for certain advantages in its use. Thus, the term "peptide" encompasses any of a variety of forms of peptide derivatives including, for example, amides, conjugates with proteins, cyclone peptides, polymerized peptides, conservatively substituted variants, analogs, fragments, chemically modified peptides, and peptide mimetics. Any peptide derivative that has desired binding characteristics of a binding domain according to the present invention can be used in the practice of the present invention. For example, a chemical group, added to the N-terminal amino acid of a synthetic peptide to block chemical reactivity of that amino terminus of the peptide, comprises an N-terminal group. Such N-terminal groups for protecting the amino terminus of a peptide are well known in the art, and include, but are not limited to, lower alkanoyl groups, acyl groups, sulfonyl groups, and carbamate forming groups. Preferred N-terminal groups may include acetyl, Fmoc, and Boc. A chemical group, added to the C-terminal amino acid of a synthetic peptide to block chemical reactivity of that carboxy terminus of the peptide, comprises a C-terminal group. Such C-terminal groups for protecting the carboxy terminus of a peptide are well known in the art, and include, but are not limited to, an ester or amide group. Terminal modifications of a peptide are often useful to reduce susceptibility by proteinase digestion, and to therefore prolong a half-life of peptides in the presence of biological fluids where proteases can be present. Optionally, a peptide comprising a binding domain, as described herein, can comprise one or more amino acids that have been modified to contain one or more chemical groups (e.g., reactive functionalities such as fluorine, bromine, or iodine) to facilitate linking the peptide to a linker molecule. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH).

Peptides which are useful as binding domains according to the present invention also include peptides having one or more substitutions, additions and/or deletions of residues relative to the sequence of an exemplary peptide disclosed in any one or more of Tables 1, 2 and 3 and SEQ ID NOs: 1-133 herein, so long as the binding properties of the original exemplary peptide are substantially retained. Thus, binding domain according to the present invention includes peptides that differ from the exemplary sequences disclosed herein by about 1, 2, 3, 4, 5, 6, 7, 8, 9, 10, 11, 12, 13, 14, 15, 16, 17, 18, 19, or 20 amino acids (and depending on the length of the exemplary peptide; also expressed in percent, for example, between 5% and 95% of the amino acid sequence of an exemplary peptide may be modified, as shown in Tables 1-3), but that substantially retain the ability of the corresponding exemplary sequence to bind to a particular material or to act as a binding domain with binding specificity as described herein (e.g., retains at least 25%, 50%, 75%, 100% or more of the binding specificity of an exemplary sequence disclosed herein, as measured using an appropriate assay). That is, binding domains according to the present invention preferably include peptides that share sequence identity with the exemplary sequences disclosed herein of at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity may be calculated manually or it may be calculated using a computer implementation of a mathematical algorithm, for example, GAP, BESTFIT, BLAST, FASTA, and TFASTA, or other programs or methods known in the art. Alignments using these programs can be performed using the default parameters.

For example, consider surface-binding domains comprising amino acid sequences identified in Table 1 as SEQ ID NOs: 18, 19, and 21. A consensus sequence may be written (using standard single letter amino acid designations) as: FZXZXXYXBXXXL, wherein Z is either F or S, X is any amino acid, and B is H or M. Thus, these amino acid sequences share sequence identity that ranges from about 20% to about 30%, yet substantially retain binding specificity for polystyrene. In another example, surface-binding domains comprising amino acid sequences identified in Table 1 as SEQ ID NOs: 44 and 45 share sequence identity greater than 80%. In yet another example, a peptide comprising an amino acid sequence set forth in SEQ ID NO:73 was modified by substitution of the two cysteine residues within the amino acid sequence with another amino acid (e.g., serine) to result in a peptide comprising an amino acid sequence set forth in SEQ ID NO:74. Binding affinity studies showed that the surface-binding domain comprising an amino acid sequence as set forth in SEQ ID NO:74 substantially retained binding specificity (demonstrating only a 10 fold reduction in binding affinity) as compared to a surface-binding domain comprising an amino acid sequence set forth in SEQ ID NO:73.

A peptide having an amino acid sequence substantially identical to a sequence of an exemplary peptide disclosed herein may have one or more different amino acid residues as a result of substituting an amino acid residue in the sequence of the exemplary peptide with a functionally similar amino acid residue (a "conservative substitution"); provided that peptide containing a conservative substitution will substantially retain the binding specificity of the exemplary peptide not containing the conservative substitution. Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue such as aspartic acid or glutamic acid for another.

[End of formal definition section]

The present invention provides for a biofunctional coating composition (or interfacial biomaterial) comprising at least surface-binding domain linked to at least one antimicrobial-binding domain. The biofunctional coating may further comprise at least one antimicrobial-binding domain bound to one or more antimicrobial compositions. The at least one surface-binding domain is in an amount effective to mediate the binding of the biofunctional coating composition to the selected surface of the medical device for which the at least one surface-binding domain has binding specificity; and the at least one antimicrobial-binding domain, having bound thereto an antimicrobial composition, is in an amount effective to confer antimicrobial activity to a surface of the medical device coated by a biofunctional coating composition according to the present invention. The present invention is illustrated in the following examples, which are not intended to be limiting.

EXAMPLE 1

Illustrated in this example are various methods for producing the biofunctional coating compositions according to the present invention. Many of the peptides comprising the binding domains in the biofunctional coating composition according to the present invention (i.e., a surface-binding domain and an antimicrobial-binding domain) were developed using phage display technology. Phage display technology is well-known in the art, and can be used to identify additional peptides for use as binding domains in the interfacial binding materials according to the present invention. In general, using phage display, a library of diverse peptides can be presented to a target substrate, and peptides that specifically bind to the substrate can be selected for use as binding domains. Multiple serial rounds of selection, called "panning," may be used. As is known in the art, any one of a variety of libraries and panning methods can be employed to identify a binding domain that is useful in a biofunctional coating composition according to the present invention. Panning methods can include, for example, solution phase screening, solid phase screening, or cell-based screening. Once a candidate binding domain is identified, directed or random mutagenesis of the sequence may be used to optimize the binding properties (including one or more of specificity and avidity) of the binding domain. For example, a variety of different phage display libraries were screened for peptides that bind to a selected target substrate (e.g., a substrate selected to find a binding domain useful in the present invention). The substrate was either bound to or placed in (depending on the selected substrate) the wells of a 96 well microtiter plate. After overnight incubation at 4° C., the nonspecific binding sites on the well surface of the polystyrene microtiter plate were blocked with a buffer containing 1% bovine serum albumin. The plates were incubated for 1 hour at room temperature with shaking at 50 rpm. The wells were then washed 5 times with a buffer containing phosphate buffered saline with Tween™ ("PBS-T"). Each library was diluted in PBS-T and added at a concentration of $10^{10}$ pfu/ml in a total volume of 100 µl. After 3 hour of incubation at room temperature with shaking at 50 rpm, unbound phage was removed by multiple washes with PBS-T. Bound phage was recovered by denaturation with 0.1 M glycine buffer, pH 2.2. The eluted phage was neutralized with phosphate buffer, and then added to E. coli cells in growth media. The cell and phage-containing media was cultured by incubation overnight at 37° C. in a shaker at 200 rpm. Phage-containing supernatant was harvested from the culture after centrifuging the culture. Second and third rounds of selection were performed in a similar manner to that of the first round of selection, using the amplified phage from the previous round as input. To detect phage that specifically bind to the selected substrate, enzyme-linked immunosorbent (ELISA-type) assays were performed using an anti-phage antibody conjugated to a detector molecule, followed by the detection and quantitation of the amount of detector molecule bound in the assay. The DNA sequence encoding peptides from the phage that specifically binds to the selected substrate was then determined; i.e., the sequence encoding the peptide is located as an insert in the phage genome, and can be sequenced to yield the corresponding amino acid sequence displayed on the phage surface.

As a specific illustrative example, titanium (in percent: Ti6Al4V) beads of approximately 5/32 of an inch diameter were washed with 70% ethanol, 40% nitric acid, distilled water, 70% ethanol, and acetone to remove any surface contaminants. One titanium bead was placed per well of 96-well polypropylene plate. Nonspecific binding sites on the titanium and the surface of the polypropylene were blocked with 1% bovine serum albumin (BSA) in PBS. The plate was incubated for 1 hour at room temperature with shaking at 50 rpm. The wells were then washed 5 times with 300 µl of PBS. Each library was diluted in PBS +1% BSA and was added at a concentration of $10^{10}$ pfu/ml in a total volume of 250 µl. After a 3-hour incubation at room temperature and shaking at 50 rpm, unbound phage were removed by washing 3 time with 300 µl of PBS-T. To recover the phage bound to the titanium beads, bound phage were released by treating with 50 mM glycine, pH 2 for 10 minutes followed by a 10 minute treatment with 100 mM ethanolamine, pH 12. The eluted phage were pooled, neutralized with 200 µl of 200 mM $NaPO_4$ pH 7. The eluted phage and the beads were added directly to E. coli DH5αF' cells in 2×YT media. The mixture was incubated overnight in a 37° C. shaker at 210 rpm. Phage supernatant was then harvested after spinning at 8500xg for 10 minutes. Second and third rounds of selection were performed in a similar manner to that of the first round, using the 50 µl of amplified phage from the previous round as input diluted with 200 µl of PBS+1% BSA. The fourth round of selection was carried out in a similar fashion; however, the washes were modified. After a 4 hour binding reaction, the beads were washed five times with PBS-T, the beads were moved to a clean polypropylene plate with 2 ml wells, 1 ml of PBS+ 1% BSA was added to each well and the washing was incubated overnight at room temperature with shaking at 50 rpm. The next morning the phage were eluted and amplified in the same manner described for rounds 1-3. Individual clonal phage were then isolated and tested by plating out dilutions of phage pools to obtain single plaques. To detect phage that specifically bound to titanium, conventional ELISAs were performed using an anti-M13 phage antibody conjugated to horseradish-peroxidase, followed by the addition of chromogenic agent ABTS (2, 2'-azinobis(3-ethylbenzthiazoline-6-sulfonic acid). Relative binding strengths of the phage were determined by testing serial dilutions of the phage for binding to titanium in an ELISA. The DNA sequence encoding peptides that specifically bound titanium was determined. The sequence encoding the peptide insert was located in the phage genome and translated to yield the corresponding amino acid sequence displayed on the phage surface.

Relative binding strengths of the peptides were determined by testing serial dilutions of the phage for binding to the selected substrate (as compared to a substrate used as a negative control; i.e., a substrate other than the selected substrate). Plotting the absorbance observed across the concentration range for each peptide sequence yielded a binding curve and rough dissociation constant ("$K_D$") of the peptides to its target substrate. The goal of the screenings and selections is to identify one or more peptides that bind to the selected substrate with an affinity in the nanomolar range (<1μM). As a specific example, titanium beads were blocked with 1% BSA in PBS for 30 minutes at room temperature. Stock solutions of each peptide being tested for binding affinity for titanium was prepared by dissolving 1-2 mg peptide in water. The final concentration of each peptide was determined using the optical density at 280 nm and the extinction coefficient for each peptide containing one or more of a tryptophan or tyrosine, and by a weight percent method for all other peptides. The peptides were prepared at 200 μM. A dilution series was then prepared for each peptide sample. Each peptide underwent a threefold dilution in 1% BSA in PBS. The peptides were incubated with the titanium beads for 1 hour at room temperature. Beads were then washed two times with PBS-T. Streptavidin-alkaline phosphatase was then added to the beads at a dilution of 1:500, and incubated for 30 minutes at room temperature. Beads were washed two times with PBS-T. PNPP (p-nitrophenyl phosphate) was used to develop the assay, and the absorbance was recorded at 405 nm. An estimate of the relative affinity of a peptide for titanium can be made by determining the concentration of peptide that gives one-half the maximal signal in the assay.

As known to those skilled in the art and methods known in the art, peptides may be synthesized by any method for peptide synthesis including, but not limited to, solid phase synthesis, solution phase synthesis, and a combination thereof. For example, peptides comprising binding domains useful in the present invention were synthesized on a peptide synthesizer using standard solid-phase synthesis techniques, and using standard FMOC peptide chemistry. After all residues were coupled, simultaneous cleavage and side chain deprotection was performed using standard methods and reagents known in the art. After cleavage from the resin, the peptides were precipitated, and the precipitate was lyophilized. The peptides were then purified using reverse-phase high performance liquid chromatography; and peptide identity was confirmed with mass spectrometry.

In some instances, the peptides comprised modifications; i.e., were blocked at the N-terminus and/or at the C-terminus, and/or were linked to another peptide. Using these methods, for example, a binding domain of a selected binding specificity (e.g., to a surface of a medical device) may be linked to another binding domain having a different binding specificity (e.g., to an antimicrobial composition) in forming a biofunctional coating composition according to the present invention. As apparent to one skilled in the art, a method of preference for linking a linker molecule to a binding domain will vary according to the reactive groups present on each molecule. Protocols for linking two molecules using reactive groups are well known to one of skill in the art. As previously described herein, using methods well known to those skilled in the art, two binding domains may be coupled by a linker to form a biofunctional coating composition according to the present invention by synthesizing a single contiguous peptide comprising a first binding domain (e.g., a surface-binding domain), a linker comprising 3 or more amino acids (e.g., GSSGK), and a second binding domain (e.g., comprising an antimicrobial-binding domain). The terms "first" and "second" are only used for purposes of ease of description, and is not intended to be construed as to limiting the order of the synthesis. In other words, the first binding domain may comprise an antimicrobial-binding domain, and the second binding domain may comprise the surface-binding domain. In an alternate method, at least one first binding domain having been avidinated (using streptavidin, avidin, or a functional derivative thereof, and methods known in the art) may be coupled to at least one second binding domain having been biotinylated (using biotin, and methods known in the art), in forming a biofunctional coating composition according to the present invention. In this example, the avidin-biotin molecules serve as the linker for coupling at least one surface-binding domain to at least one antimicrobial-binding domain in forming an interfacial biomaterial according to the present invention.

EXAMPLE 2

This example illustrates peptides comprising surface-binding domains which may be used in the biofunctional coating compositions according to the present invention. As described herein in more detail, a surface-binding domain is a peptide that specifically binds to the surface of a medical device. In that regard, a surface-binding domain may bind to any material which is used to make a medical device, and comprises a surface of the medical device, wherein the material may be selected from the group consisting of a metal, a metal oxide, a non-metal oxide, a ceramic, a polymer (such as, for example, a synthetic polymer such as a polyurethane, a rubber, a plastic, an acrylic, a silicone), and combinations thereof. Developed using the methods described in Example 1 herein, and as described in U.S. patent application Ser. No.10/300,694 (published as US 20030185870), and U.S. patent application Ser. No. 11/152,974 (published as US 20060051395) (each assigned to the present applicant; the disclosures of which are herein incorporated by reference), exemplary peptides having binding specificity for a surface of a medical device include, but are not limited to the following.

Table 1 illustrates exemplary surface-binding domains, which may be used in the biofunctional coating compositions according to the present invention, having binding specificity for a polymer, and comprising: SEQ ID NOs:1-22 that specifically bind to polystyrene; SEQ ID NO:23 that specifically binds to polyurethane; SEQ ID NOs: 24-37 that specifically binds to polyglycolic acid; SEQ ID NOs: 38-43 that specifically bind to polycarbonate; SEQ ID NOs: 44-54 that specifically bind to nylon; and SEQ ID NOs: 55 and 56 that specifically bind to teflon.

TABLE 1

| SEQ ID NO: | Amino acid sequence (single letter code) |
|---|---|
| Binding specificity for polystyrene | |
| 1 | FLSFVFPASAWGG |
| 2 | FYMPFGPTWWQHV |
| 3 | LFSWFLPTDNYPV |
| 4 | FMDIWSPWHLLGT |
| 5 | FSSLFFPHWPAQL |
| 6 | SCAMAQWFCDRAEPHHVIS |

TABLE 1-continued

| SEQ ID NO: | Amino acid sequence (single letter code) |
|---|---|
| 7 | SCNMSHLTGVSLCDSLATS |
| 8 | SCVYSFIDGSGCNSHSLGS |
| 9 | SCSGFHLLCESRSMQRELS |
| 10 | SCGILCSAFPFNNHQVGAS |
| 11 | SCCSMFFKNVSYVGASNPS |
| 12 | SCPIWKYCDDYSRSGSIFS |
| 13 | SCLFNSMKCLVLILCFVS |
| 14 | SCYVNGHNSVWVVVFWGVS |
| 15 | SCDFVCNVLFNVNHGSNMS |
| 16 | SCLNKFFVLMSVGLRSYTS |
| 17 | SCCNHNSTSVKDVQFPTLS |
| 18 | FFPSSWYSHLGVL |
| 19 | FFGFDVYDMSNAL |
| 20 | LSFSDFYFSEGSE |
| 21 | FSYSVSYAHPEGL |
| 22 | LPHLIQYRVLLVS |
| Binding specificity for polyurethane | |
| 23 | SCYVNGHNSVWVVVFWGVS |
| Binding specificity of polyglycolic acid | |
| 24 | SCNSFMFINGSFKETGGCS |
| 25 | SCFGNLGNLIYTCDRLMPS |
| 26 | SCSFFMPWCNFLNGEMAVS |
| 27 | SCFGNVFCVYNQFAAGLFS |
| 28 | SCCFINSNFSVMNHSLFKS |
| 29 | SCDYFSFLECFSNGWSGAS |
| 30 | SCWMGLFECPDAWLHDWDS |
| 31 | SCFWYSWLCSASSSDALIS |
| 32 | SCFGNFLSFGFNCESALGS |
| 33 | SCLYCHLNNQFLSWVSGNS |
| 34 | SCFGFSDCLSWFVQPSTAS |
| 35 | SCNHLGFFSSFCDRLVENS |
| 36 | SCGYFCSFYNYLDIGTASS |
| 37 | SCNSSSYSWYCWFGGSSPS |
| Binding specificity for polycarbonate | |
| 38 | FGHGWLNTLNLGW |
| 39 | FSPFSANLWYDMF |
| 40 | VFVPFGNWLSTSV |

TABLE 1-continued

| SEQ ID NO: | Amino acid sequence (single letter code) |
|---|---|
| 41 | FWNVNYNPWGWNY |
| 42 | FYWDRLNVGWGLL |
| 43 | LYSTMYPGMSWLV |
| Binding specificity for nylon | |
| 44 | MASMTGGQYMGH |
| 45 | MASMTGGQWMGH |
| 46 | SCFYQNVISSSFAGNPWEC |
| 47 | SCNMLLNSLPLPSEDWSAC |
| 48 | SCPFTHSLALNTDRASPGC |
| 49 | SCFESDFPNVRHHVLKQSC |
| 50 | SCVFDSKHFSPTHSPHDVC |
| 51 | SCGDHMTDKNMPNSGISGC |
| 52 | SCDFFNRHGYNSGCEHSVC |
| 53 | SCGDHMTDKNMPNSGISGC |
| 54 | SCYYNGLVVHHSNSGHKDC |
| Binding specificity for Teflon | |
| 55 | CWSRFRLFMLFCMFYLVS |
| 56 | CIKYPFLYCCLLSLFLFS |

Table 2 illustrates exemplary surface-binding domains, which may be used in the biofunctional coating compositions according to the present invention, having binding specificity for a metal (including a metal alloy), a metal oxide, or a non-metal oxide, and comprising: SEQ ID NOs:57-76 that specifically bind to titanium; and SEQ ID NOs: 77-94 that specifically bind to stainless steel.

TABLE 2

| SEQ ID NO: | Amino acid sequence (single letter code) |
|---|---|
| Binding specificity for titanium | |
| 57 | SCFWFLRWSLFIVLFTCCS |
| 58 | SCESVDCFADSRMAKVSMS |
| 59 | SCVGFFCITGSDVASVNSS |
| 60 | SCSDCLKSVDFIPSSLASS |
| 61 | SCAFDCPSSVARSPGEWSS |
| 62 | SCVDVMHADSPGPDGLNS |
| 63 | SCSSFEVSEMFTCAVSSYS |
| 64 | SCGLNFPLCSFVDFAQDAS |
| 65 | SCMLFSSVFDCGMLISDLS |
| 66 | SCVDYVMHADSPGPDGLNS |

TABLE 2-continued

| SEQ ID NO: | Amino acid sequence (single letter code) |
| --- | --- |
| 67 | SCSENFMFNMYGTGVCTES |
| 68 | HKHPVTPRFFVVE |
| 69 | CNCYVTPNLLKHKCYKIC |
| 70 | CSHNHHKLTAKHQVAHKC |
| 71 | CDQNDIFYTSKKSHKSHC |
| 72 | SSDVYLVSHKHHLTRHNS |
| 73 | SDKCHKHWYCYESKYGGS |
| 74 | SDKSHKHWYSYESKYGGS |
| 75 | HHKLKHQMLHLNGG |
| 76 | GHHHKKDQLPQLGG |
| Binding specificity for steel | |
| 77 | CFVLNCHLVLDRP |
| 78 | SCFGNFLSFGFNCEYALGS |
| 79 | DGFFILYKNPDVL |
| 80 | NHQNQTN |
| 81 | ATHMVGS |
| 82 | GINPNFI |
| 83 | TAISGHF |
| 84 | LYGTPEYAVQPLR |
| 85 | CFLTQDYCVLAGK |
| 86 | VLHLDSYGPSVPL |
| 87 | VVDSTGYLRPVST |
| 88 | VLQNATNVAPFVT |
| 89 | WWSSMPYVGDYTS |
| 90 | SSYFNLGLVKHNHVRHHDS |
| 91 | CHDHSNKYLKSWKHQQNC |
| 92 | SCKHDSEFIKKHVHAVKKC |
| 93 | SCHHLKHNTHKESKMHHEC |
| 94 | VNKMNRLWEPL |

While these exemplary peptide sequences are disclosed herein, one skilled in the art will appreciate that the binding properties conferred by those sequences may be attributable to only some of the amino acids comprised by the sequences. Thus, a peptide which comprises only a portion of an exemplary amino acid sequence disclosed herein may have substantially the same binding properties as the exemplary peptide comprising the full-length amino acid sequence. Thus, also useful as surface-binding domains in the biofunctional coating compositions according to the present invention are peptides that comprise only 3, 4, 5, 6, 7, 8, 9, 10, 11, or 12 of the amino acids in a particular exemplary sequence provided herein. Such amino acids may be contiguous or non-contiguous so long as the desired property (e.g., substantially retaining binding specificity for the selected material) of the surface-binding domain is retained, as determined by an appropriate assay (described herein and/or as known to those skilled in the art). Such amino acids may be concentrated at the amino-terminal end of the exemplary peptide (for example, 4 amino acids may be concentrated in the first 4, 5, 6, 7, 8, 9, 10, 11, or 12 amino acids of the peptide), at the carboxy-terminal end of the exemplary peptide, or they may be dispersed throughout the exemplary peptide (e.g., acting as specific contact points, with the material for which the peptide has binding specificity, spaced apart from each other). For example, consider surface-binding domains comprising amino acid sequences identified in Table 1 as SEQ ID NOs: 11, 18, and 19. A peptide comprising the amino acid sequence illustrated as SEQ ID NO:11, shares with SEQ ID NOs: 18 and 19 a consensus sequence of FFXXXXY (wherein X is any amino acid), except that in SEQ ID NO:11 the consensus sequence comprises amino acids internal to the amino acid sequence (e.g, between the N-terminal end and the C-terminal ends of the amino acid sequence of SEQ ID NO:11). It is also noted that in the phage display system used to identify surface-binding domains useful with the present invention, generally 2 amino acid residues (typically, serine) of phage sequence were displayed at the N-terminal end of the peptide sequence, and generally 2 amino acid residues (typically, serine and arginine) of phage sequence were displayed at the C-terminal end of the peptide sequence. While typically such phage amino acids adjoining the peptide displayed had no significant contribution to the binding specificity of the peptide, the surface-binding domains for use according to the present invention may also comprise in their amino acid sequence such phage amino acids adjoining the peptide at the N-terminus and at the C-terminus.

EXAMPLE 3

This example illustrates peptides comprising antimicrobial-binding domains which may be used in the biofunctional coating compositions according to the present invention. Developed using the methods described in Example 1 herein, Table 3 illustrates exemplary peptides having binding specificity for an antimicrobial composition comprising amino acid sequences comprising: SEQ ID NOs:95-127 that specifically bind to vancomycin; and SEQ ID NOs: 128-133 that specifically bind to gentamycin.

TABLE 3

| SEQ ID NO: | Amino acid sequence (single letter code) |
| --- | --- |
| Binding specificity for vancomycin | |
| 95 | SFSLSPSFNWRLSSFSSP |
| 96 | SCPGWGDWGRSSGVGWFGS |
| 97 | SCFISPSSLPYESLRELGVS |
| 98 | SCFSFFPSSPWGGASHSPSS |
| 99 | SFDLLFDHYYKSNR |
| 100 | SCDFQKVPYSWPQVPPALLS |
| 101 | SFSYSYSHPYWWQS |
| 102 | SFISFGHGSIAVW |

TABLE 3-continued

| SEQ ID NO: | Amino acid sequence (single letter code) |
|---|---|
| 103 | SFFDSGYHWTNYSP |
| 104 | SFFVLPDHARNALF |
| 105 | SFFGRFHSEPMMV |
| 106 | SFFDSDSHVFRWRA |
| 107 | SVFALYPHALKKFE |
| 108 | SSVFFQYHGMPMVH |
| 109 | SFSHFYLHSVGAPT |
| 110 | SFDRIFSHLGHLES |
| 111 | SFSNSYVHNMASVW |
| 112 | SCDRLQNFKTHDVLVPTRC |
| 113 | SCLSGLPFFPWDLENRALAC |
| 114 | SGAEAFSSGSASWAGGWV |
| 115 | SFVGFSAVSSSVAGAASW |
| 116 | SFFVSSSSLFGSVASGGA |
| 117 | SFWGAGFSASSAVAGAVA |
| 118 | SCFFNSSKDMDGPKSWRMC |
| 119 | SCNFEEYAEKDPPRNFKWC |
| 120 | SCNSFETLRTQVLKSPLSC |
| 121 | SCDIWQSNYASPIRPGQKC |
| 122 | SCPNWIQGKLSVTNYDSRC |
| 123 | SSSHFGNDFVKSWKIAVGS |
| 124 | SSFLNWKSHTQVYKSWGQS |
| 125 | SSNHYHAVTSMRGSDIMRS |
| 126 | SSPHLWPWADSNVFGDSRS |
| 127 | SSASSSLLDFSFDFGLP |
| Binding specificity for gentamycin | |
| 128 | SFSFLFVASSSFAGSAAG |
| 129 | SFFFVSVGMVQPSL |
| 130 | STVDSLLLCCTFVAEN |
| 131 | SIFCSSYSGFAVLASEFS |
| 132 | SASVAGSFSGEVGGVGGF |
| 133 | SSASSSLLDFSFDFGLP |

While these exemplary peptide sequences are disclosed herein, one of skill will appreciate that the binding properties conferred by those sequences may be attributable to only some of the amino acids (e.g., 3 or more) comprised by the sequences. Thus, a peptide which comprises only a portion (e.g., between 3 and 10 amino acid residues) of an exemplary amino acid sequence disclosed herein may have substantially the same binding properties as the exemplary peptide comprising the full-length amino acid sequence. Thus, also useful as antimicrobial-binding domains in the biofunctional coating compositions according to the present invention are peptides that comprise only 3, 4, 5, 6, 7, 8, 9, 10, 11, or 12 of the amino acids in a particular exemplary sequence provided herein. Such amino acids may be contiguous or non-contiguous so long as the desired property (e.g., substantially retaining binding specificity for the selected antimicrobial composition) of the antimicrobial-binding domain is retained as determined by an appropriate assay (described herein and/or as known to those skilled in the art). Such amino acids may be concentrated at the amino-terminal end of the exemplary peptide (for example, 4 amino acids may be concentrated in the first 4, 5, 6, 7, 8, 9, 10, 11, or 12 amino acids of the peptide), at the carboxy-terminal end of the exemplary peptide, or they may be dispersed throughout the exemplary peptide (e.g., acting as specific contact points spaced apart from each other). For example, in referring to Table 3, compare antimicrobial-binding domains comprising peptides comprising amino acid sequences identified as SEQ ID NO:95, 97, and 104 which share a consensus sequence of SJXXXP as N-terminal amino acid sequence of the peptide, wherein J is either C or F, and X is any amino acid. It is also noted that in the phage display system used to identify antimicrobial-binding domains useful with the present invention, generally 2 amino acid residues (typically, serine) of phage sequence were displayed at the N-terminal end of the peptide sequence, and generally 2 amino acid residues (typically, serine and arginine) of phage sequence were displayed at the C-terminal end of the peptide sequence. While typically such phage amino acids adjoining the peptide displayed had no significant contribution to the binding specificity of the peptide, the antimicrobial-binding domains for use according to the present invention may also comprise amino acid sequences which include such phage amino acids adjoining the peptide at the N-terminus and at the C-terminus.

EXAMPLE 4

In this example, illustrated are methods according to the present invention: (a) a method for manufacturing a medical device; and (b) a method of forming a coating on a surface of a medical device, the coating imparting antimicrobial acitivity to the surface, wherein the surface being suitable for contacting biological tissue, biological fluids, or a combination thereof. The methods comprise contacting at least one surface of a medical device with an effective amount of a biofunctional coating composition under conditions suitable to produce a coating on the surface, wherein the biofunctional coating composition comprises at least one surface-binding domain and at least one antimicrobial-binding domain, and wherein the at least one surface-binding domain is linked to the at least one antimicrobial-binding domain by a linker. Preferably, the at least one surface-binding domain is covalently coupled to the at least one antimicrobial-binding domain via a linker. The at least one surface-binding domain is the component of the biofunctional coating composition which is primarily responsible for binding the biofunctional coating composition to the one or more surfaces of the medical device to be coated.

With respect to these methods according to the present invention, and with respect to a biofunctional coating composition according to the present invention, and wherein at least one surface of the medical device to be coated comprises more than one material (e.g., two different metals; a metal and a metal oxide; a metal alloy and a polymer; two different polymers; and the like), the at least one surface-binding domain in the biofunctional coating may comprise a plurality (two or more) of types of surface-binding domains, wherein each type of surface-binding domain has binding specificity for a different surface material to be coated as compared to the other surface-binding domains of which the biofunctional coating composition is comprised. Also with respect to this method according to the present invention, and with respect to a biofunctional coating composition according to the present invention, the at least one antimicrobial-binding domain may comprise a plurality of types of antimicrobial-binding domains (e.g., two or more different peptides, each with binding specificity for a different antimicrobial composition as compared to the compared to the other antimicrobial-binding domains of which the biofunctional coating composition is comprised). For example, it may be advantageous to have a biofunctional coating composition, or one or more surfaces of a medical device coated with the biofunctional coating composition, having more than one type of antimicrobial-binding domain associated therewith so as to result in a combination of antimicrobial compositions (e.g., selected from a single class of antimicrobial compositions, or selected from different classes of antimicrobial compositions).

In these methods according to the present invention, when the biofunctional coating composition is contacted with the at least one surface of the medical device to be coated, either (a) the at least one antimicrobial-binding domain is bound to one or more antimicrobial compositions; or (b) the at least one antimicrobial-binding domain is not yet bound to one or more antimicrobial compositions. With respect to the latter, in a further step of coating, the coated surface of the medical device is then contacted with an effective amount of one or more antimicrobial compositions, for which the at least one antimicrobial-binding domain has binding specificity, under conditions suitable so that the one or more antimicrobial compositions bind to the at least one antimicrobial-binding domain.

Conventional processes known in the art may be used to apply the biofunctional coating according to the present invention to the one or more surfaces of the medical device to be coated. Such processes are known to include, but are not limited to, dipping, brushing, spraying, vapor deposition, and electro-deposition. Formulations of the biofunctional coating composition according to the present invention may depend on the process used for coating the medical device. For example, a solution or suspension comprising the biofunctional coating composition may be applied through the spray nozzle of a spraying device, creating droplets that coat the surface of the medical device to be coated. The medical device is allowed to dry, and may then be further processed prior to use (e.g., washed in a solution (e.g., water or isotonic buffer) to remove excess biofunctional coating composition; by sterilization using any one or methods known in the art for sterilizing medical devices; etc.). Alternatively, the biofunctional coating composition and the medical device may all be sterilized prior to the process, and the process performed under sterile conditions.

In another process for applying the biofunctional coating to one or more surfaces of a medical device to be coated, the surface of the medical device to be coated is dipped into a liquid (e.g., solution or suspension, aqueous or solvent) containing the biofunctional coating composition in an amount effective to coat the surface. For example, the surface is dipped or immersed into a bath containing the biofunctional coating composition. Suitable conditions for applying the biofunctional coating composition include allowing the surface to be coated to remain in contact with the liquid containing the biofunctional coating composition for a suitable period of time (e.g., ranging from about 5 minutes to about 12 hours; more preferably, ranging from 15 minutes to 60 minutes), at a suitable temperature (e.g., ranging from 10° C. to about 50° C.; more preferably, ranging from room temperature to 37° C.). The coated medical device may then be further processed, as necessary for use (washing, sterilization, and the like).

In another process for applying the biofunctional coating to one or more surfaces of a medical device to be coated, the biofunctional coating composition according to the present invention is formulated in a dry powder (e.g., via air drying or lyophilizing the biofunctional coating composition). The powder comprising the biofunctional coating composition is then applied using methods known in the art for powder-coating the surface of the medical device to be coated. Typically, once applied, such powder coatings are then heat-treated (e.g., using infrared heating means) to compete the application process.

However, these illustrative processes for applying a biofunctional coating composition to a surface of a medical device are not exclusive, as other coating and stabilization methods may be employed (as one of skill in the art will be able to select the compositions and methods used to fit the needs of the particular device and purpose). For example, where the surface of the medical device to be coated is metallic in nature, a hydrophilic polymer (as previously described herein in more detail) may be used in conjunction (either applied simultaneously, or subsequently, to application of the biofunctional coating composition according to the present invention) so long as the biofunctional coating composition on the surface of the medical device substantially retains its function to confer antimicrobial activity on the surface. In continuing this illustration, because of the elastomeric nature of the hydrophilic polymer, it may add to the stability of the biofunctional coating composition bound to the surface of the medical device should the device be subjected to mechanical forces or stress.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept; and thus, such modifications and/or adaptations are intended to be within the meaning and scope of the appended claims.

What is claimed is:

1. A medical device comprising at least one surface coated with a coating for imparting antimicrobial activity to the medical device, wherein the coating comprises a surface-binding domain coupled to an antimicrobial-binding domain, wherein the surface-binding domain comprises a peptide that binds non-covalently to a material of which the medical device is comprised, and wherein the antimicrobial-binding domain comprises a peptide that binds non-covalently to an antibiotic composition.

2. The medical device according to claim 1, wherein the material to which the surface-binding domain binds comprises a material selected from the group consisting of metal, metal oxide, non-metal oxide, ceramic, polymer, and a combination thereof.

3. The medical device according to claim 1, wherein the coating comprises more than one type of surface-binding domain for binding to more than one type of surface material of the medical device.

4. The medical device according to claim 1, wherein the antimicrobial-binding domain is bound to the antibiotic composition.

5. The medical device according to claim 1, wherein the coating comprises more than one type of antimicrobial-binding domain for binding to more than one type of antibiotic composition.

6. The medical device according to claim 1, wherein the surface-binding domain is coupled to the antimicrobial-binding domain via a linker.

7. The medical device according to claim 1, wherein the surface-binding domain comprises a peptide consisting of 12 to 20 amino acids in length and, optionally, is modified at one or more amino acids with a chemical group, and wherein the antimicrobial-binding domain comprises a peptide consisting of 13 to 20 amino acids in length and, optionally, is modified at one or more amino acids with a chemical group.

8. The medical device of claim 1, wherein the antibiotic composition comprises vancomycin.

9. A method for manufacturing a medical device according to claim 1, the method comprising contacting a medical device with an effective amount of a coating to produce a medical device having at least one surface coated by the coating; wherein the coating comprises a surface-binding domain coupled to an antimicrobial-binding domain; wherein the surface-binding domain comprises a peptide that binds non-covalently to a material of which the medical device is comprised, and the antimicrobial-binding domain comprises a peptide that binds non-covalently to an antibiotic composition.

10. The method according to claim 9, wherein the antimicrobial-binding domain is bound to the antibiotic composition.

11. The method according to claim 9, wherein the coating comprises more than one type of antimicrobial-binding domain for binding to more than one type of antibiotic composition.

12. The method according to claim 9, wherein the coating comprises more than one type of surface-binding domain for binding to more than one type of surface material of the medical device.

13. The method according to claim 9, wherein the material to which the surface-binding domain binds comprises a material selected from the group consisting of a metal, a metal oxide, a non-metal oxide, a ceramic, a polymer, and a combination thereof.

14. The method according to claim 9, wherein the surface-binding domain is coupled to the antimicrobial-binding domain via a linker.

15. The method of claim 9, wherein the antibiotic composition comprises vancomycin.

* * * * *

SEQUENCE LISTING

<160> NUMBER OF SEQ ID NOS: 133

<210> SEQ ID NO 1
<211> LENGTH: 13
<212> TYPE: PRT
<213> ORGANISM: Artificial
<220> FEATURE:
<223> OTHER INFORMATION: synthesized

<400> SEQUENCE: 1

```
Phe Leu Ser Phe Val Phe Pro Ala Ser Ala Trp Gly Gly
1               5                   10

<210> SEQ ID NO 2
<211> LENGTH: 13
<212> TYPE: PRT
<213> ORGANISM: Artificial
<220> FEATURE:
<223> OTHER INFORMATION: synthesized

<400> SEQUENCE: 2

Phe Tyr Met Pro Phe Gly Pro Thr Trp Trp Gln His Val
1               5                   10

<210> SEQ ID NO 3
<211> LENGTH: 13
<212> TYPE: PRT
<213> ORGANISM: Artificial
<220> FEATURE:
<223> OTHER INFORMATION: synthesized

<400> SEQUENCE: 3

Leu Phe Ser Trp Phe Leu Pro Thr Asp Asn Tyr Pro Val
1               5                   10

<210> SEQ ID NO 4
<211> LENGTH: 13
<212> TYPE: PRT
<213> ORGANISM: Artificial
<220> FEATURE:
<223> OTHER INFORMATION: synthesized

<400> SEQUENCE: 4

Phe Met Asp Ile Trp Ser Pro Trp His Leu Leu Gly Thr
1               5                   10

<210> SEQ ID NO 5
<211> LENGTH: 13
<212> TYPE: PRT
<213> ORGANISM: Artificial
<220> FEATURE:
<223> OTHER INFORMATION: synthesized

<400> SEQUENCE: 5

Phe Ser Ser Leu Phe Phe Pro His Trp Pro Ala Gln Leu
1               5                   10

<210> SEQ ID NO 6
<211> LENGTH: 19
<212> TYPE: PRT
<213> ORGANISM: Artificial
<220> FEATURE:
<223> OTHER INFORMATION: synthesized

<400> SEQUENCE: 6

Ser Cys Ala Met Ala Gln Trp Phe Cys Asp Arg Ala Glu Pro His His
1               5                   10                  15

Val Ile Ser

<210> SEQ ID NO 7
<211> LENGTH: 19
<212> TYPE: PRT
<213> ORGANISM: Artificial
<220> FEATURE:
<223> OTHER INFORMATION: synthesized
```

```
<400> SEQUENCE: 7

Ser Cys Asn Met Ser His Leu Thr Gly Val Ser Leu Cys Asp Ser Leu
1               5                   10                  15

Ala Thr Ser

<210> SEQ ID NO 8
<211> LENGTH: 19
<212> TYPE: PRT
<213> ORGANISM: Artificial
<220> FEATURE:
<223> OTHER INFORMATION: synthesized

<400> SEQUENCE: 8

Ser Cys Val Tyr Ser Phe Ile Asp Gly Ser Gly Cys Asn Ser His Ser
1               5                   10                  15

Leu Gly Ser

<210> SEQ ID NO 9
<211> LENGTH: 19
<212> TYPE: PRT
<213> ORGANISM: Artificial
<220> FEATURE:
<223> OTHER INFORMATION: synthesized

<400> SEQUENCE: 9

Ser Cys Ser Gly Phe His Leu Leu Cys Glu Ser Arg Ser Met Gln Arg
1               5                   10                  15

Glu Leu Ser

<210> SEQ ID NO 10
<211> LENGTH: 19
<212> TYPE: PRT
<213> ORGANISM: Artificial
<220> FEATURE:
<223> OTHER INFORMATION: synthesized

<400> SEQUENCE: 10

Ser Cys Gly Ile Leu Cys Ser Ala Phe Pro Phe Asn Asn His Gln Val
1               5                   10                  15

Gly Ala Ser

<210> SEQ ID NO 11
<211> LENGTH: 19
<212> TYPE: PRT
<213> ORGANISM: Artificial
<220> FEATURE:
<223> OTHER INFORMATION: synthesized

<400> SEQUENCE: 11

Ser Cys Cys Ser Met Phe Phe Lys Asn Val Ser Tyr Val Gly Ala Ser
1               5                   10                  15

Asn Pro Ser

<210> SEQ ID NO 12
<211> LENGTH: 19
<212> TYPE: PRT
<213> ORGANISM: Artificial
<220> FEATURE:
<223> OTHER INFORMATION: synthesized

<400> SEQUENCE: 12

Ser Cys Pro Ile Trp Lys Tyr Cys Asp Asp Tyr Ser Arg Ser Gly Ser
1               5                   10                  15
```

-continued

Ile Phe Ser

<210> SEQ ID NO 13
<211> LENGTH: 18
<212> TYPE: PRT
<213> ORGANISM: Artificial
<220> FEATURE:
<223> OTHER INFORMATION: synthesized

<400> SEQUENCE: 13

Ser Cys Leu Phe Asn Ser Met Lys Cys Leu Val Leu Ile Leu Cys Phe
1               5                   10                  15

Val Ser

<210> SEQ ID NO 14
<211> LENGTH: 19
<212> TYPE: PRT
<213> ORGANISM: Artificial
<220> FEATURE:
<223> OTHER INFORMATION: synthesized

<400> SEQUENCE: 14

Ser Cys Tyr Val Asn Gly His Asn Ser Val Trp Val Val Phe Trp
1               5                   10                  15

Gly Val Ser

<210> SEQ ID NO 15
<211> LENGTH: 19
<212> TYPE: PRT
<213> ORGANISM: Artificial
<220> FEATURE:
<223> OTHER INFORMATION: synthesized

<400> SEQUENCE: 15

Ser Cys Asp Phe Val Cys Asn Val Leu Phe Asn Val Asn His Gly Ser
1               5                   10                  15

Asn Met Ser

<210> SEQ ID NO 16
<211> LENGTH: 19
<212> TYPE: PRT
<213> ORGANISM: Artificial
<220> FEATURE:
<223> OTHER INFORMATION: synthesized

<400> SEQUENCE: 16

Ser Cys Leu Asn Lys Phe Phe Val Leu Met Ser Val Gly Leu Arg Ser
1               5                   10                  15

Tyr Thr Ser

<210> SEQ ID NO 17
<211> LENGTH: 19
<212> TYPE: PRT
<213> ORGANISM: Artificial
<220> FEATURE:
<223> OTHER INFORMATION: synthesized

<400> SEQUENCE: 17

Ser Cys Cys Asn His Asn Ser Thr Ser Val Lys Asp Val Gln Phe Pro
1               5                   10                  15

Thr Leu Ser

```
<210> SEQ ID NO 18
<211> LENGTH: 13
<212> TYPE: PRT
<213> ORGANISM: Artificial
<220> FEATURE:
<223> OTHER INFORMATION: synthesized

<400> SEQUENCE: 18

Phe Phe Pro Ser Ser Trp Tyr Ser His Leu Gly Val Leu
1               5                   10

<210> SEQ ID NO 19
<211> LENGTH: 13
<212> TYPE: PRT
<213> ORGANISM: Artificial
<220> FEATURE:
<223> OTHER INFORMATION: synthesized

<400> SEQUENCE: 19

Phe Phe Gly Phe Asp Val Tyr Asp Met Ser Asn Ala Leu
1               5                   10

<210> SEQ ID NO 20
<211> LENGTH: 13
<212> TYPE: PRT
<213> ORGANISM: Artificial
<220> FEATURE:
<223> OTHER INFORMATION: synthesized

<400> SEQUENCE: 20

Leu Ser Phe Ser Asp Phe Tyr Phe Ser Glu Gly Ser Glu
1               5                   10

<210> SEQ ID NO 21
<211> LENGTH: 13
<212> TYPE: PRT
<213> ORGANISM: Artificial
<220> FEATURE:
<223> OTHER INFORMATION: synthesized

<400> SEQUENCE: 21

Phe Ser Tyr Ser Val Ser Tyr Ala His Pro Glu Gly Leu
1               5                   10

<210> SEQ ID NO 22
<211> LENGTH: 13
<212> TYPE: PRT
<213> ORGANISM: Artificial
<220> FEATURE:
<223> OTHER INFORMATION: synthesized

<400> SEQUENCE: 22

Leu Pro His Leu Ile Gln Tyr Arg Val Leu Leu Val Ser
1               5                   10

<210> SEQ ID NO 23
<211> LENGTH: 19
<212> TYPE: PRT
<213> ORGANISM: Artificial
<220> FEATURE:
<223> OTHER INFORMATION: synthesized

<400> SEQUENCE: 23

Ser Cys Tyr Val Asn Gly His Asn Ser Val Trp Val Val Phe Trp
1               5                   10                  15

Gly Val Ser
```

```
<210> SEQ ID NO 24
<211> LENGTH: 19
<212> TYPE: PRT
<213> ORGANISM: Artificial
<220> FEATURE:
<223> OTHER INFORMATION: synthesized

<400> SEQUENCE: 24

Ser Cys Asn Ser Phe Met Phe Ile Asn Gly Ser Phe Lys Glu Thr Gly
1               5                   10                  15

Gly Cys Ser

<210> SEQ ID NO 25
<211> LENGTH: 19
<212> TYPE: PRT
<213> ORGANISM: Artificial
<220> FEATURE:
<223> OTHER INFORMATION: synthesized

<400> SEQUENCE: 25

Ser Cys Phe Gly Asn Leu Gly Asn Leu Ile Tyr Thr Cys Asp Arg Leu
1               5                   10                  15

Met Pro Ser

<210> SEQ ID NO 26
<211> LENGTH: 19
<212> TYPE: PRT
<213> ORGANISM: Artificial
<220> FEATURE:
<223> OTHER INFORMATION: synthesized

<400> SEQUENCE: 26

Ser Cys Ser Phe Phe Met Pro Trp Cys Asn Phe Leu Asn Gly Glu Met
1               5                   10                  15

Ala Val Ser

<210> SEQ ID NO 27
<211> LENGTH: 19
<212> TYPE: PRT
<213> ORGANISM: Artificial
<220> FEATURE:
<223> OTHER INFORMATION: synthesized

<400> SEQUENCE: 27

Ser Cys Phe Gly Asn Val Phe Cys Val Tyr Asn Gln Phe Ala Ala Gly
1               5                   10                  15

Leu Phe Ser

<210> SEQ ID NO 28
<211> LENGTH: 19
<212> TYPE: PRT
<213> ORGANISM: Artificial
<220> FEATURE:
<223> OTHER INFORMATION: synthesized

<400> SEQUENCE: 28

Ser Cys Cys Phe Ile Asn Ser Asn Phe Ser Val Met Asn His Ser Leu
1               5                   10                  15

Phe Lys Ser

<210> SEQ ID NO 29
<211> LENGTH: 19
<212> TYPE: PRT
```

<213> ORGANISM: Artificial
<220> FEATURE:
<223> OTHER INFORMATION: synthesized

<400> SEQUENCE: 29

Ser Cys Asp Tyr Phe Ser Phe Leu Glu Cys Phe Ser Asn Gly Trp Ser
1               5                   10                  15

Gly Ala Ser

<210> SEQ ID NO 30
<211> LENGTH: 19
<212> TYPE: PRT
<213> ORGANISM: Artificial
<220> FEATURE:
<223> OTHER INFORMATION: synthesized

<400> SEQUENCE: 30

Ser Cys Trp Met Gly Leu Phe Glu Cys Pro Asp Ala Trp Leu His Asp
1               5                   10                  15

Trp Asp Ser

<210> SEQ ID NO 31
<211> LENGTH: 19
<212> TYPE: PRT
<213> ORGANISM: Artificial
<220> FEATURE:
<223> OTHER INFORMATION: synthesized

<400> SEQUENCE: 31

Ser Cys Phe Trp Tyr Ser Trp Leu Cys Ser Ala Ser Ser Ser Asp Ala
1               5                   10                  15

Leu Ile Ser

<210> SEQ ID NO 32
<211> LENGTH: 19
<212> TYPE: PRT
<213> ORGANISM: Artificial
<220> FEATURE:
<223> OTHER INFORMATION: synthesized

<400> SEQUENCE: 32

Ser Cys Phe Gly Asn Phe Leu Ser Phe Gly Phe Asn Cys Glu Ser Ala
1               5                   10                  15

Leu Gly Ser

<210> SEQ ID NO 33
<211> LENGTH: 19
<212> TYPE: PRT
<213> ORGANISM: Artificial
<220> FEATURE:
<223> OTHER INFORMATION: synthesized

<400> SEQUENCE: 33

Ser Cys Leu Tyr Cys His Leu Asn Asn Gln Phe Leu Ser Trp Val Ser
1               5                   10                  15

Gly Asn Ser

<210> SEQ ID NO 34
<211> LENGTH: 19
<212> TYPE: PRT
<213> ORGANISM: Artificial
<220> FEATURE:
<223> OTHER INFORMATION: synthesized -continued

```
<400> SEQUENCE: 34

Ser Cys Phe Gly Phe Ser Asp Cys Leu Ser Trp Phe Val Gln Pro Ser
1               5                   10                  15

Thr Ala Ser

<210> SEQ ID NO 35
<211> LENGTH: 19
<212> TYPE: PRT
<213> ORGANISM: Artificial
<220> FEATURE:
<223> OTHER INFORMATION: synthesized

<400> SEQUENCE: 35

Ser Cys Asn His Leu Gly Phe Phe Ser Phe Cys Asp Arg Leu Val
1               5                   10                  15

Glu Asn Ser

<210> SEQ ID NO 36
<211> LENGTH: 19
<212> TYPE: PRT
<213> ORGANISM: Artificial
<220> FEATURE:
<223> OTHER INFORMATION: synthesized

<400> SEQUENCE: 36

Ser Cys Gly Tyr Phe Cys Ser Phe Tyr Asn Tyr Leu Asp Ile Gly Thr
1               5                   10                  15

Ala Ser Ser

<210> SEQ ID NO 37
<211> LENGTH: 19
<212> TYPE: PRT
<213> ORGANISM: Artificial
<220> FEATURE:
<223> OTHER INFORMATION: synthesized

<400> SEQUENCE: 37

Ser Cys Asn Ser Ser Ser Tyr Ser Trp Tyr Cys Trp Phe Gly Gly Ser
1               5                   10                  15

Ser Pro Ser

<210> SEQ ID NO 38
<211> LENGTH: 13
<212> TYPE: PRT
<213> ORGANISM: Artificial
<220> FEATURE:
<223> OTHER INFORMATION: synthesized

<400> SEQUENCE: 38

Phe Gly His Gly Trp Leu Asn Thr Leu Asn Leu Gly Trp
1               5                   10

<210> SEQ ID NO 39
<211> LENGTH: 13
<212> TYPE: PRT
<213> ORGANISM: Artificial
<220> FEATURE:
<223> OTHER INFORMATION: synthesized

<400> SEQUENCE: 39

Phe Ser Pro Phe Ser Ala Asn Leu Trp Tyr Asp Met Phe
1               5                   10
```

<210> SEQ ID NO 40
<211> LENGTH: 13
<212> TYPE: PRT
<213> ORGANISM: Artificial
<220> FEATURE:
<223> OTHER INFORMATION: synthesized

<400> SEQUENCE: 40

Val Phe Val Pro Phe Gly Asn Trp Leu Ser Thr Ser Val
1               5                   10

<210> SEQ ID NO 41
<211> LENGTH: 13
<212> TYPE: PRT
<213> ORGANISM: Artificial
<220> FEATURE:
<223> OTHER INFORMATION: synthesized

<400> SEQUENCE: 41

Phe Trp Asn Val Asn Tyr Asn Pro Trp Gly Trp Asn Tyr
1               5                   10

<210> SEQ ID NO 42
<211> LENGTH: 13
<212> TYPE: PRT
<213> ORGANISM: Artificial
<220> FEATURE:
<223> OTHER INFORMATION: synthesized

<400> SEQUENCE: 42

Phe Tyr Trp Asp Arg Leu Asn Val Gly Trp Gly Leu Leu
1               5                   10

<210> SEQ ID NO 43
<211> LENGTH: 13
<212> TYPE: PRT
<213> ORGANISM: Artificial
<220> FEATURE:
<223> OTHER INFORMATION: synthesized

<400> SEQUENCE: 43

Leu Tyr Ser Thr Met Tyr Pro Gly Met Ser Trp Leu Val
1               5                   10

<210> SEQ ID NO 44
<211> LENGTH: 12
<212> TYPE: PRT
<213> ORGANISM: Artificial
<220> FEATURE:
<223> OTHER INFORMATION: synthesized

<400> SEQUENCE: 44

Met Ala Ser Met Thr Gly Gly Gln Tyr Met Gly His
1               5                   10

<210> SEQ ID NO 45
<211> LENGTH: 12
<212> TYPE: PRT
<213> ORGANISM: Artificial
<220> FEATURE:
<223> OTHER INFORMATION: synthesized

<400> SEQUENCE: 45

Met Ala Ser Met Thr Gly Gly Gln Trp Met Gly His
1               5                   10

<210> SEQ ID NO 46

-continued

```
<211> LENGTH: 19
<212> TYPE: PRT
<213> ORGANISM: Artificial
<220> FEATURE:
<223> OTHER INFORMATION: synthesized

<400> SEQUENCE: 46

Ser Cys Phe Tyr Gln Asn Val Ile Ser Ser Phe Ala Gly Asn Pro
1               5                   10                  15

Trp Glu Cys

<210> SEQ ID NO 47
<211> LENGTH: 19
<212> TYPE: PRT
<213> ORGANISM: Artificial
<220> FEATURE:
<223> OTHER INFORMATION: synthesized

<400> SEQUENCE: 47

Ser Cys Asn Met Leu Leu Asn Ser Leu Pro Leu Pro Ser Glu Asp Trp
1               5                   10                  15

Ser Ala Cys

<210> SEQ ID NO 48
<211> LENGTH: 19
<212> TYPE: PRT
<213> ORGANISM: Artificial
<220> FEATURE:
<223> OTHER INFORMATION: synthesized

<400> SEQUENCE: 48

Ser Cys Pro Phe Thr His Ser Leu Ala Leu Asn Thr Asp Arg Ala Ser
1               5                   10                  15

Pro Gly Cys

<210> SEQ ID NO 49
<211> LENGTH: 19
<212> TYPE: PRT
<213> ORGANISM: Artificial
<220> FEATURE:
<223> OTHER INFORMATION: synthesized

<400> SEQUENCE: 49

Ser Cys Phe Glu Ser Asp Phe Pro Asn Val Arg His His Val Leu Lys
1               5                   10                  15

Gln Ser Cys

<210> SEQ ID NO 50
<211> LENGTH: 19
<212> TYPE: PRT
<213> ORGANISM: Artificial
<220> FEATURE:
<223> OTHER INFORMATION: synthesized

<400> SEQUENCE: 50

Ser Cys Val Phe Asp Ser Lys His Phe Ser Pro Thr His Ser Pro His
1               5                   10                  15

Asp Val Cys

<210> SEQ ID NO 51
<211> LENGTH: 19
<212> TYPE: PRT
<213> ORGANISM: Artificial
<220> FEATURE:
```

<223> OTHER INFORMATION: synthesized

<400> SEQUENCE: 51

Ser Cys Gly Asp His Met Thr Asp Lys Asn Met Pro Asn Ser Gly Ile
1               5                   10                  15

Ser Gly Cys

<210> SEQ ID NO 52
<211> LENGTH: 19
<212> TYPE: PRT
<213> ORGANISM: Artificial
<220> FEATURE:
<223> OTHER INFORMATION: synthesized

<400> SEQUENCE: 52

Ser Cys Asp Phe Phe Asn Arg His Gly Tyr Asn Ser Gly Cys Glu His
1               5                   10                  15

Ser Val Cys

<210> SEQ ID NO 53
<211> LENGTH: 19
<212> TYPE: PRT
<213> ORGANISM: Artificial
<220> FEATURE:
<223> OTHER INFORMATION: synthesized

<400> SEQUENCE: 53

Ser Cys Gly Asp His Met Thr Asp Lys Asn Met Pro Asn Ser Gly Ile
1               5                   10                  15

Ser Gly Cys

<210> SEQ ID NO 54
<211> LENGTH: 19
<212> TYPE: PRT
<213> ORGANISM: Artificial
<220> FEATURE:
<223> OTHER INFORMATION: synthesized

<400> SEQUENCE: 54

Ser Cys Tyr Tyr Asn Gly Leu Val Val His His Ser Asn Ser Gly His
1               5                   10                  15

Lys Asp Cys

<210> SEQ ID NO 55
<211> LENGTH: 18
<212> TYPE: PRT
<213> ORGANISM: Artificial
<220> FEATURE:
<223> OTHER INFORMATION: synthesized

<400> SEQUENCE: 55

Cys Trp Ser Arg Phe Arg Leu Phe Met Leu Phe Cys Met Phe Tyr Leu
1               5                   10                  15

Val Ser

<210> SEQ ID NO 56
<211> LENGTH: 18
<212> TYPE: PRT
<213> ORGANISM: Artificial
<220> FEATURE:
<223> OTHER INFORMATION: synthesized

<400> SEQUENCE: 56

```
Cys Ile Lys Tyr Pro Phe Leu Tyr Cys Cys Leu Leu Ser Leu Phe Leu
1               5                   10                  15

Phe Ser

<210> SEQ ID NO 57
<211> LENGTH: 19
<212> TYPE: PRT
<213> ORGANISM: Artificial
<220> FEATURE:
<223> OTHER INFORMATION: synthesized

<400> SEQUENCE: 57

Ser Cys Phe Trp Phe Leu Arg Trp Ser Leu Phe Ile Val Leu Phe Thr
1               5                   10                  15

Cys Cys Ser

<210> SEQ ID NO 58
<211> LENGTH: 19
<212> TYPE: PRT
<213> ORGANISM: Artificial
<220> FEATURE:
<223> OTHER INFORMATION: synthesized

<400> SEQUENCE: 58

Ser Cys Glu Ser Val Asp Cys Phe Ala Asp Ser Arg Met Ala Lys Val
1               5                   10                  15

Ser Met Ser

<210> SEQ ID NO 59
<211> LENGTH: 19
<212> TYPE: PRT
<213> ORGANISM: Artificial
<220> FEATURE:
<223> OTHER INFORMATION: synthesized

<400> SEQUENCE: 59

Ser Cys Val Gly Phe Phe Cys Ile Thr Gly Ser Asp Val Ala Ser Val
1               5                   10                  15

Asn Ser Ser

<210> SEQ ID NO 60
<211> LENGTH: 19
<212> TYPE: PRT
<213> ORGANISM: Artificial
<220> FEATURE:
<223> OTHER INFORMATION: synthesized

<400> SEQUENCE: 60

Ser Cys Ser Asp Cys Leu Lys Ser Val Asp Phe Ile Pro Ser Ser Leu
1               5                   10                  15

Ala Ser Ser

<210> SEQ ID NO 61
<211> LENGTH: 19
<212> TYPE: PRT
<213> ORGANISM: Artificial
<220> FEATURE:
<223> OTHER INFORMATION: synthesized

<400> SEQUENCE: 61

Ser Cys Ala Phe Asp Cys Pro Ser Ser Val Ala Arg Ser Pro Gly Glu
1               5                   10                  15

Trp Ser Ser
```

```
<210> SEQ ID NO 62
<211> LENGTH: 18
<212> TYPE: PRT
<213> ORGANISM: Artificial
<220> FEATURE:
<223> OTHER INFORMATION: synthesized

<400> SEQUENCE: 62

Ser Cys Val Asp Val Met His Ala Asp Ser Pro Gly Pro Asp Gly Leu
1               5                   10                  15

Asn Ser

<210> SEQ ID NO 63
<211> LENGTH: 19
<212> TYPE: PRT
<213> ORGANISM: Artificial
<220> FEATURE:
<223> OTHER INFORMATION: synthesized

<400> SEQUENCE: 63

Ser Cys Ser Ser Phe Glu Val Ser Glu Met Phe Thr Cys Ala Val Ser
1               5                   10                  15

Ser Tyr Ser

<210> SEQ ID NO 64
<211> LENGTH: 19
<212> TYPE: PRT
<213> ORGANISM: Artificial
<220> FEATURE:
<223> OTHER INFORMATION: synthesized

<400> SEQUENCE: 64

Ser Cys Gly Leu Asn Phe Pro Leu Cys Ser Phe Val Asp Phe Ala Gln
1               5                   10                  15

Asp Ala Ser

<210> SEQ ID NO 65
<211> LENGTH: 19
<212> TYPE: PRT
<213> ORGANISM: Artificial
<220> FEATURE:
<223> OTHER INFORMATION: synthesized

<400> SEQUENCE: 65

Ser Cys Met Leu Phe Ser Ser Val Phe Asp Cys Gly Met Leu Ile Ser
1               5                   10                  15

Asp Leu Ser

<210> SEQ ID NO 66
<211> LENGTH: 19
<212> TYPE: PRT
<213> ORGANISM: Artificial
<220> FEATURE:
<223> OTHER INFORMATION: synthesized

<400> SEQUENCE: 66

Ser Cys Val Asp Tyr Val Met His Ala Asp Ser Pro Gly Pro Asp Gly
1               5                   10                  15

Leu Asn Ser

<210> SEQ ID NO 67
<211> LENGTH: 19
```

```
<212> TYPE: PRT
<213> ORGANISM: Artificial
<220> FEATURE:
<223> OTHER INFORMATION: synthesized

<400> SEQUENCE: 67

Ser Cys Ser Glu Asn Phe Met Phe Asn Met Tyr Gly Thr Gly Val Cys
1               5                   10                  15

Thr Glu Ser

<210> SEQ ID NO 68
<211> LENGTH: 13
<212> TYPE: PRT
<213> ORGANISM: Artificial
<220> FEATURE:
<223> OTHER INFORMATION: synthesized

<400> SEQUENCE: 68

His Lys His Pro Val Thr Pro Arg Phe Phe Val Val Glu
1               5                   10

<210> SEQ ID NO 69
<211> LENGTH: 18
<212> TYPE: PRT
<213> ORGANISM: Artificial
<220> FEATURE:
<223> OTHER INFORMATION: synthesized

<400> SEQUENCE: 69

Cys Asn Cys Tyr Val Thr Pro Asn Leu Leu Lys His Lys Cys Tyr Lys
1               5                   10                  15

Ile Cys

<210> SEQ ID NO 70
<211> LENGTH: 18
<212> TYPE: PRT
<213> ORGANISM: Artificial
<220> FEATURE:
<223> OTHER INFORMATION: synthesized

<400> SEQUENCE: 70

Cys Ser His Asn His His Lys Leu Thr Ala Lys His Gln Val Ala His
1               5                   10                  15

Lys Cys

<210> SEQ ID NO 71
<211> LENGTH: 18
<212> TYPE: PRT
<213> ORGANISM: Artificial
<220> FEATURE:
<223> OTHER INFORMATION: synthesized

<400> SEQUENCE: 71

Cys Asp Gln Asn Asp Ile Phe Tyr Thr Ser Lys Lys Ser His Lys Ser
1               5                   10                  15

His Cys

<210> SEQ ID NO 72
<211> LENGTH: 18
<212> TYPE: PRT
<213> ORGANISM: Artificial
<220> FEATURE:
<223> OTHER INFORMATION: synthesized

<400> SEQUENCE: 72
```

```
Ser Ser Asp Val Tyr Leu Val Ser His Lys His His Leu Thr Arg His
1               5                   10                  15

Asn Ser

<210> SEQ ID NO 73
<211> LENGTH: 18
<212> TYPE: PRT
<213> ORGANISM: Artificial
<220> FEATURE:
<223> OTHER INFORMATION: synthesized

<400> SEQUENCE: 73

Ser Asp Lys Cys His Lys His Trp Tyr Cys Tyr Glu Ser Lys Tyr Gly
1               5                   10                  15

Gly Ser

<210> SEQ ID NO 74
<211> LENGTH: 18
<212> TYPE: PRT
<213> ORGANISM: Artificial
<220> FEATURE:
<223> OTHER INFORMATION: synthesized

<400> SEQUENCE: 74

Ser Asp Lys Ser His Lys His Trp Tyr Ser Tyr Glu Ser Lys Tyr Gly
1               5                   10                  15

Gly Ser

<210> SEQ ID NO 75
<211> LENGTH: 14
<212> TYPE: PRT
<213> ORGANISM: Artificial
<220> FEATURE:
<223> OTHER INFORMATION: synthesized

<400> SEQUENCE: 75

His His Lys Leu Lys His Gln Met Leu His Leu Asn Gly Gly
1               5                   10

<210> SEQ ID NO 76
<211> LENGTH: 14
<212> TYPE: PRT
<213> ORGANISM: Artificial
<220> FEATURE:
<223> OTHER INFORMATION: synthesized

<400> SEQUENCE: 76

Gly His His His Lys Lys Asp Gln Leu Pro Gln Leu Gly Gly
1               5                   10

<210> SEQ ID NO 77
<211> LENGTH: 13
<212> TYPE: PRT
<213> ORGANISM: Artificial
<220> FEATURE:
<223> OTHER INFORMATION: synthesized

<400> SEQUENCE: 77

Cys Phe Val Leu Asn Cys His Leu Val Leu Asp Arg Pro
1               5                   10

<210> SEQ ID NO 78
<211> LENGTH: 19
<212> TYPE: PRT
```

<213> ORGANISM: Artificial
<220> FEATURE:
<223> OTHER INFORMATION: synthesized

<400> SEQUENCE: 78

```
Ser Cys Phe Gly Asn Phe Leu Ser Phe Gly Phe Asn Cys Glu Tyr Ala
1               5                   10                  15

Leu Gly Ser
```

<210> SEQ ID NO 79
<211> LENGTH: 13
<212> TYPE: PRT
<213> ORGANISM: Artificial
<220> FEATURE:
<223> OTHER INFORMATION: synthesized

<400> SEQUENCE: 79

```
Asp Gly Phe Phe Ile Leu Tyr Lys Asn Pro Asp Val Leu
1               5                   10
```

<210> SEQ ID NO 80
<211> LENGTH: 7
<212> TYPE: PRT
<213> ORGANISM: Artificial
<220> FEATURE:
<223> OTHER INFORMATION: synthesized

<400> SEQUENCE: 80

```
Asn His Gln Asn Gln Thr Asn
1               5
```

<210> SEQ ID NO 81
<211> LENGTH: 7
<212> TYPE: PRT
<213> ORGANISM: Artificial
<220> FEATURE:
<223> OTHER INFORMATION: synthesized

<400> SEQUENCE: 81

```
Ala Thr His Met Val Gly Ser
1               5
```

<210> SEQ ID NO 82
<211> LENGTH: 7
<212> TYPE: PRT
<213> ORGANISM: Artificial
<220> FEATURE:
<223> OTHER INFORMATION: synthesized

<400> SEQUENCE: 82

```
Gly Ile Asn Pro Asn Phe Ile
1               5
```

<210> SEQ ID NO 83
<211> LENGTH: 7
<212> TYPE: PRT
<213> ORGANISM: Artificial
<220> FEATURE:
<223> OTHER INFORMATION: synthesized

<400> SEQUENCE: 83

```
Thr Ala Ile Ser Gly His Phe
1               5
```

<210> SEQ ID NO 84
<211> LENGTH: 13

-continued

```
<212> TYPE: PRT
<213> ORGANISM: Artificial
<220> FEATURE:
<223> OTHER INFORMATION: synthesized

<400> SEQUENCE: 84

Leu Tyr Gly Thr Pro Glu Tyr Ala Val Gln Pro Leu Arg
1               5                   10

<210> SEQ ID NO 85
<211> LENGTH: 13
<212> TYPE: PRT
<213> ORGANISM: Artificial
<220> FEATURE:
<223> OTHER INFORMATION: synthesized

<400> SEQUENCE: 85

Cys Phe Leu Thr Gln Asp Tyr Cys Val Leu Ala Gly Lys
1               5                   10

<210> SEQ ID NO 86
<211> LENGTH: 13
<212> TYPE: PRT
<213> ORGANISM: Artificial
<220> FEATURE:
<223> OTHER INFORMATION: synthesized

<400> SEQUENCE: 86

Val Leu His Leu Asp Ser Tyr Gly Pro Ser Val Pro Leu
1               5                   10

<210> SEQ ID NO 87
<211> LENGTH: 13
<212> TYPE: PRT
<213> ORGANISM: Artificial
<220> FEATURE:
<223> OTHER INFORMATION: synthesized

<400> SEQUENCE: 87

Val Val Asp Ser Thr Gly Tyr Leu Arg Pro Val Ser Thr
1               5                   10

<210> SEQ ID NO 88
<211> LENGTH: 13
<212> TYPE: PRT
<213> ORGANISM: Artificial
<220> FEATURE:
<223> OTHER INFORMATION: synthesized

<400> SEQUENCE: 88

Val Leu Gln Asn Ala Thr Asn Val Ala Pro Phe Val Thr
1               5                   10

<210> SEQ ID NO 89
<211> LENGTH: 13
<212> TYPE: PRT
<213> ORGANISM: Artificial
<220> FEATURE:
<223> OTHER INFORMATION: synthesized

<400> SEQUENCE: 89

Trp Trp Ser Ser Met Pro Tyr Val Gly Asp Tyr Thr Ser
1               5                   10

<210> SEQ ID NO 90
<211> LENGTH: 19
<212> TYPE: PRT
```

<213> ORGANISM: Artificial
<220> FEATURE:
<223> OTHER INFORMATION: synthesized

<400> SEQUENCE: 90

```
Ser Ser Tyr Phe Asn Leu Gly Leu Val Lys His Asn His Val Arg His
1               5                   10                  15
His Asp Ser
```

<210> SEQ ID NO 91
<211> LENGTH: 18
<212> TYPE: PRT
<213> ORGANISM: Artificial
<220> FEATURE:
<223> OTHER INFORMATION: synthesized

<400> SEQUENCE: 91

```
Cys His Asp His Ser Asn Lys Tyr Leu Lys Ser Trp Lys His Gln Gln
1               5                   10                  15
Asn Cys
```

<210> SEQ ID NO 92
<211> LENGTH: 19
<212> TYPE: PRT
<213> ORGANISM: Artificial
<220> FEATURE:
<223> OTHER INFORMATION: synthesized

<400> SEQUENCE: 92

```
Ser Cys Lys His Asp Ser Glu Phe Ile Lys Lys His Val His Ala Val
1               5                   10                  15
Lys Lys Cys
```

<210> SEQ ID NO 93
<211> LENGTH: 19
<212> TYPE: PRT
<213> ORGANISM: Artificial
<220> FEATURE:
<223> OTHER INFORMATION: synthesized

<400> SEQUENCE: 93

```
Ser Cys His His Leu Lys His Asn Thr His Lys Glu Ser Lys Met His
1               5                   10                  15
His Glu Cys
```

<210> SEQ ID NO 94
<211> LENGTH: 11
<212> TYPE: PRT
<213> ORGANISM: Artificial
<220> FEATURE:
<223> OTHER INFORMATION: synthesized

<400> SEQUENCE: 94

```
Val Asn Lys Met Asn Arg Leu Trp Glu Pro Leu
1               5                   10
```

<210> SEQ ID NO 95
<211> LENGTH: 18
<212> TYPE: PRT
<213> ORGANISM: Artificial
<220> FEATURE:
<223> OTHER INFORMATION: synthesized

<400> SEQUENCE: 95

-continued

Ser Phe Ser Leu Ser Pro Ser Phe Asn Trp Arg Leu Ser Ser Phe Ser
1               5                   10                  15

Ser Pro

<210> SEQ ID NO 96
<211> LENGTH: 20
<212> TYPE: PRT
<213> ORGANISM: Artificial
<220> FEATURE:
<223> OTHER INFORMATION: synthesized

<400> SEQUENCE: 96

Ser Cys Pro Gly Trp Gly Asp Trp Gly Arg Ser Ser Gly Val Gly Val
1               5                   10                  15

Val Phe Gly Ser
            20

<210> SEQ ID NO 97
<211> LENGTH: 20
<212> TYPE: PRT
<213> ORGANISM: Artificial
<220> FEATURE:
<223> OTHER INFORMATION: synthesized

<400> SEQUENCE: 97

Ser Cys Phe Ile Ser Pro Ser Ser Leu Pro Tyr Glu Ser Leu Arg Glu
1               5                   10                  15

Leu Gly Val Ser
            20

<210> SEQ ID NO 98
<211> LENGTH: 20
<212> TYPE: PRT
<213> ORGANISM: Artificial
<220> FEATURE:
<223> OTHER INFORMATION: synthesized

<400> SEQUENCE: 98

Ser Cys Phe Ser Phe Phe Pro Ser Ser Pro Trp Gly Gly Ala Ser His
1               5                   10                  15

Ser Pro Ser Ser
            20

<210> SEQ ID NO 99
<211> LENGTH: 14
<212> TYPE: PRT
<213> ORGANISM: Artificial
<220> FEATURE:
<223> OTHER INFORMATION: synthesized

<400> SEQUENCE: 99

Ser Phe Asp Leu Leu Phe Asp His Tyr Tyr Lys Ser Asn Arg
1               5                   10

<210> SEQ ID NO 100
<211> LENGTH: 20
<212> TYPE: PRT
<213> ORGANISM: Artificial
<220> FEATURE:
<223> OTHER INFORMATION: synthesized

<400> SEQUENCE: 100

Ser Cys Asp Phe Gln Lys Val Pro Tyr Ser Trp Pro Gln Val Pro Pro
1               5                   10                  15

Ala Leu Leu Ser
            20

<210> SEQ ID NO 101
<211> LENGTH: 14
<212> TYPE: PRT
<213> ORGANISM: Artificial
<220> FEATURE:
<223> OTHER INFORMATION: synthesized

<400> SEQUENCE: 101

Ser Phe Ser Tyr Ser Tyr Ser His Pro Tyr Trp Trp Gln Ser
1               5                   10

<210> SEQ ID NO 102
<211> LENGTH: 13
<212> TYPE: PRT
<213> ORGANISM: Artificial
<220> FEATURE:
<223> OTHER INFORMATION: synthesized

<400> SEQUENCE: 102

Ser Phe Ile Ser Phe Gly His Gly Ser Ile Ala Val Trp
1               5                   10

<210> SEQ ID NO 103
<211> LENGTH: 14
<212> TYPE: PRT
<213> ORGANISM: Artificial
<220> FEATURE:
<223> OTHER INFORMATION: synthesized

<400> SEQUENCE: 103

Ser Phe Phe Asp Ser Gly Tyr His Trp Thr Asn Tyr Ser Pro
1               5                   10

<210> SEQ ID NO 104
<211> LENGTH: 14
<212> TYPE: PRT
<213> ORGANISM: Artificial
<220> FEATURE:
<223> OTHER INFORMATION: synthesized

<400> SEQUENCE: 104

Ser Phe Phe Val Leu Pro Asp His Ala Arg Asn Ala Leu Phe
1               5                   10

<210> SEQ ID NO 105
<211> LENGTH: 13
<212> TYPE: PRT
<213> ORGANISM: Artificial
<220> FEATURE:
<223> OTHER INFORMATION: synthesized

<400> SEQUENCE: 105

Ser Phe Phe Gly Arg Phe His Ser Glu Pro Met Met Val
1               5                   10

<210> SEQ ID NO 106
<211> LENGTH: 14
<212> TYPE: PRT
<213> ORGANISM: Artificial
<220> FEATURE:
<223> OTHER INFORMATION: synthesized

<400> SEQUENCE: 106

Ser Phe Phe Asp Ser Asp Ser His Val Phe Arg Trp Arg Ala

```
<210> SEQ ID NO 107
<211> LENGTH: 14
<212> TYPE: PRT
<213> ORGANISM: Artificial
<220> FEATURE:
<223> OTHER INFORMATION: synthesized

<400> SEQUENCE: 107

Ser Val Phe Ala Leu Tyr Pro His Ala Leu Lys Lys Phe Glu
1               5                   10

<210> SEQ ID NO 108
<211> LENGTH: 14
<212> TYPE: PRT
<213> ORGANISM: Artificial
<220> FEATURE:
<223> OTHER INFORMATION: synthesized

<400> SEQUENCE: 108

Ser Ser Val Phe Phe Gln Tyr His Gly Met Pro Met Val His
1               5                   10

<210> SEQ ID NO 109
<211> LENGTH: 14
<212> TYPE: PRT
<213> ORGANISM: Artificial
<220> FEATURE:
<223> OTHER INFORMATION: synthesized

<400> SEQUENCE: 109

Ser Phe Ser His Phe Tyr Leu His Ser Val Gly Ala Pro Thr
1               5                   10

<210> SEQ ID NO 110
<211> LENGTH: 14
<212> TYPE: PRT
<213> ORGANISM: Artificial
<220> FEATURE:
<223> OTHER INFORMATION: synthesized

<400> SEQUENCE: 110

Ser Phe Asp Arg Ile Phe Ser His Leu Gly His Leu Glu Ser
1               5                   10

<210> SEQ ID NO 111
<211> LENGTH: 14
<212> TYPE: PRT
<213> ORGANISM: Artificial
<220> FEATURE:
<223> OTHER INFORMATION: synthesized

<400> SEQUENCE: 111

Ser Phe Ser Asn Ser Tyr Val His Asn Met Ala Ser Val Trp
1               5                   10

<210> SEQ ID NO 112
<211> LENGTH: 19
<212> TYPE: PRT
<213> ORGANISM: Artificial
<220> FEATURE:
<223> OTHER INFORMATION: synthesized

<400> SEQUENCE: 112

Ser Cys Asp Arg Leu Gln Asn Phe Lys Thr His Asp Val Leu Val Pro
1               5                   10                  15
```

Thr Arg Cys

<210> SEQ ID NO 113
<211> LENGTH: 20
<212> TYPE: PRT
<213> ORGANISM: Artificial
<220> FEATURE:
<223> OTHER INFORMATION: synthesized

<400> SEQUENCE: 113

Ser Cys Leu Ser Gly Leu Pro Phe Phe Pro Trp Asp Leu Glu Asn Arg
1               5                   10                  15

Ala Leu Ala Cys
            20

<210> SEQ ID NO 114
<211> LENGTH: 18
<212> TYPE: PRT
<213> ORGANISM: Artificial
<220> FEATURE:
<223> OTHER INFORMATION: synthesized

<400> SEQUENCE: 114

Ser Gly Ala Glu Ala Phe Ser Ser Gly Ser Ala Ser Trp Ala Gly Gly
1               5                   10                  15

Trp Val

<210> SEQ ID NO 115
<211> LENGTH: 18
<212> TYPE: PRT
<213> ORGANISM: Artificial
<220> FEATURE:
<223> OTHER INFORMATION: synthesized

<400> SEQUENCE: 115

Ser Phe Val Gly Phe Ser Ala Val Ser Ser Val Ala Gly Ala Ala
1               5                   10                  15

Ser Trp

<210> SEQ ID NO 116
<211> LENGTH: 18
<212> TYPE: PRT
<213> ORGANISM: Artificial
<220> FEATURE:
<223> OTHER INFORMATION: synthesized

<400> SEQUENCE: 116

Ser Phe Phe Val Ser Ser Ser Ser Leu Phe Gly Ser Val Ala Ser Gly
1               5                   10                  15

Gly Ala

<210> SEQ ID NO 117
<211> LENGTH: 18
<212> TYPE: PRT
<213> ORGANISM: Artificial
<220> FEATURE:
<223> OTHER INFORMATION: synthesized

<400> SEQUENCE: 117

Ser Phe Trp Gly Ala Gly Phe Ser Ala Ser Ser Ala Val Ala Gly Ala
1               5                   10                  15

Val Ala

```
<210> SEQ ID NO 118
<211> LENGTH: 19
<212> TYPE: PRT
<213> ORGANISM: Artificial
<220> FEATURE:
<223> OTHER INFORMATION: synthesized

<400> SEQUENCE: 118

Ser Cys Phe Phe Asn Ser Ser Lys Asp Met Asp Gly Pro Lys Ser Trp
1               5                   10                  15

Arg Met Cys

<210> SEQ ID NO 119
<211> LENGTH: 19
<212> TYPE: PRT
<213> ORGANISM: Artificial
<220> FEATURE:
<223> OTHER INFORMATION: synthesized

<400> SEQUENCE: 119

Ser Cys Asn Phe Glu Glu Tyr Ala Glu Lys Asp Pro Pro Arg Asn Phe
1               5                   10                  15

Lys Trp Cys

<210> SEQ ID NO 120
<211> LENGTH: 19
<212> TYPE: PRT
<213> ORGANISM: Artificial
<220> FEATURE:
<223> OTHER INFORMATION: synthesized

<400> SEQUENCE: 120

Ser Cys Asn Ser Phe Glu Thr Leu Arg Thr Gln Val Leu Lys Ser Pro
1               5                   10                  15

Leu Ser Cys

<210> SEQ ID NO 121
<211> LENGTH: 19
<212> TYPE: PRT
<213> ORGANISM: Artificial
<220> FEATURE:
<223> OTHER INFORMATION: synthesized

<400> SEQUENCE: 121

Ser Cys Asp Ile Trp Gln Ser Asn Tyr Ala Ser Pro Ile Arg Pro Gly
1               5                   10                  15

Gln Lys Cys

<210> SEQ ID NO 122
<211> LENGTH: 19
<212> TYPE: PRT
<213> ORGANISM: Artificial
<220> FEATURE:
<223> OTHER INFORMATION: synthesized

<400> SEQUENCE: 122

Ser Cys Pro Asn Trp Ile Gln Gly Lys Leu Ser Val Thr Asn Tyr Asp
1               5                   10                  15

Ser Arg Cys

<210> SEQ ID NO 123
<211> LENGTH: 19
<212> TYPE: PRT
```

```
<213> ORGANISM: Artificial
<220> FEATURE:
<223> OTHER INFORMATION: synthesized

<400> SEQUENCE: 123

Ser Ser Ser His Phe Gly Asn Asp Phe Val Lys Ser Trp Lys Ile Ala
1               5                   10                  15
Val Gly Ser

<210> SEQ ID NO 124
<211> LENGTH: 19
<212> TYPE: PRT
<213> ORGANISM: Artificial
<220> FEATURE:
<223> OTHER INFORMATION: synthesized

<400> SEQUENCE: 124

Ser Ser Phe Leu Asn Trp Lys Ser His Thr Gln Val Tyr Lys Ser Trp
1               5                   10                  15
Gly Gln Ser

<210> SEQ ID NO 125
<211> LENGTH: 19
<212> TYPE: PRT
<213> ORGANISM: Artificial
<220> FEATURE:
<223> OTHER INFORMATION: synthesized

<400> SEQUENCE: 125

Ser Ser Asn His Tyr His Ala Val Thr Ser Met Arg Gly Ser Asp Ile
1               5                   10                  15
Met Arg Ser

<210> SEQ ID NO 126
<211> LENGTH: 19
<212> TYPE: PRT
<213> ORGANISM: Artificial
<220> FEATURE:
<223> OTHER INFORMATION: synthesized

<400> SEQUENCE: 126

Ser Ser Pro His Leu Trp Pro Trp Ala Asp Ser Asn Val Phe Gly Asp
1               5                   10                  15
Ser Arg Ser

<210> SEQ ID NO 127
<211> LENGTH: 17
<212> TYPE: PRT
<213> ORGANISM: Artificial
<220> FEATURE:
<223> OTHER INFORMATION: synthesized

<400> SEQUENCE: 127

Ser Ser Ala Ser Ser Ser Leu Leu Asp Phe Ser Phe Asp Phe Gly Leu
1               5                   10                  15
Pro

<210> SEQ ID NO 128
<211> LENGTH: 18
<212> TYPE: PRT
<213> ORGANISM: Artificial
<220> FEATURE:
<223> OTHER INFORMATION: synthesized
```

```
<400> SEQUENCE: 128

Ser Phe Ser Phe Leu Phe Val Ala Ser Ser Phe Ala Gly Ser Ala
1               5                   10                  15

Ala Gly

<210> SEQ ID NO 129
<211> LENGTH: 14
<212> TYPE: PRT
<213> ORGANISM: Artificial
<220> FEATURE:
<223> OTHER INFORMATION: synthesized

<400> SEQUENCE: 129

Ser Phe Phe Phe Val Ser Val Gly Met Val Gln Pro Ser Leu
1               5                   10

<210> SEQ ID NO 130
<211> LENGTH: 16
<212> TYPE: PRT
<213> ORGANISM: Artificial
<220> FEATURE:
<223> OTHER INFORMATION: synthesized

<400> SEQUENCE: 130

Ser Thr Val Asp Ser Leu Leu Leu Cys Cys Thr Phe Val Ala Glu Asn
1               5                   10                  15

<210> SEQ ID NO 131
<211> LENGTH: 18
<212> TYPE: PRT
<213> ORGANISM: Artificial
<220> FEATURE:
<223> OTHER INFORMATION: synthesized

<400> SEQUENCE: 131

Ser Ile Phe Cys Ser Ser Tyr Ser Gly Phe Ala Val Leu Ala Ser Glu
1               5                   10                  15

Phe Ser

<210> SEQ ID NO 132
<211> LENGTH: 18
<212> TYPE: PRT
<213> ORGANISM: Artificial
<220> FEATURE:
<223> OTHER INFORMATION: synthesized

<400> SEQUENCE: 132

Ser Ala Ser Val Ala Gly Ser Phe Ser Gly Glu Val Gly Gly Val Gly
1               5                   10                  15

Gly Phe

<210> SEQ ID NO 133
<211> LENGTH: 17
<212> TYPE: PRT
<213> ORGANISM: Artificial
<220> FEATURE:
<223> OTHER INFORMATION: synthesized

<400> SEQUENCE: 133

Ser Ser Ala Ser Ser Ser Leu Leu Asp Phe Ser Phe Asp Phe Gly Leu
1               5                   10                  15

Pro
```